Figure 3:
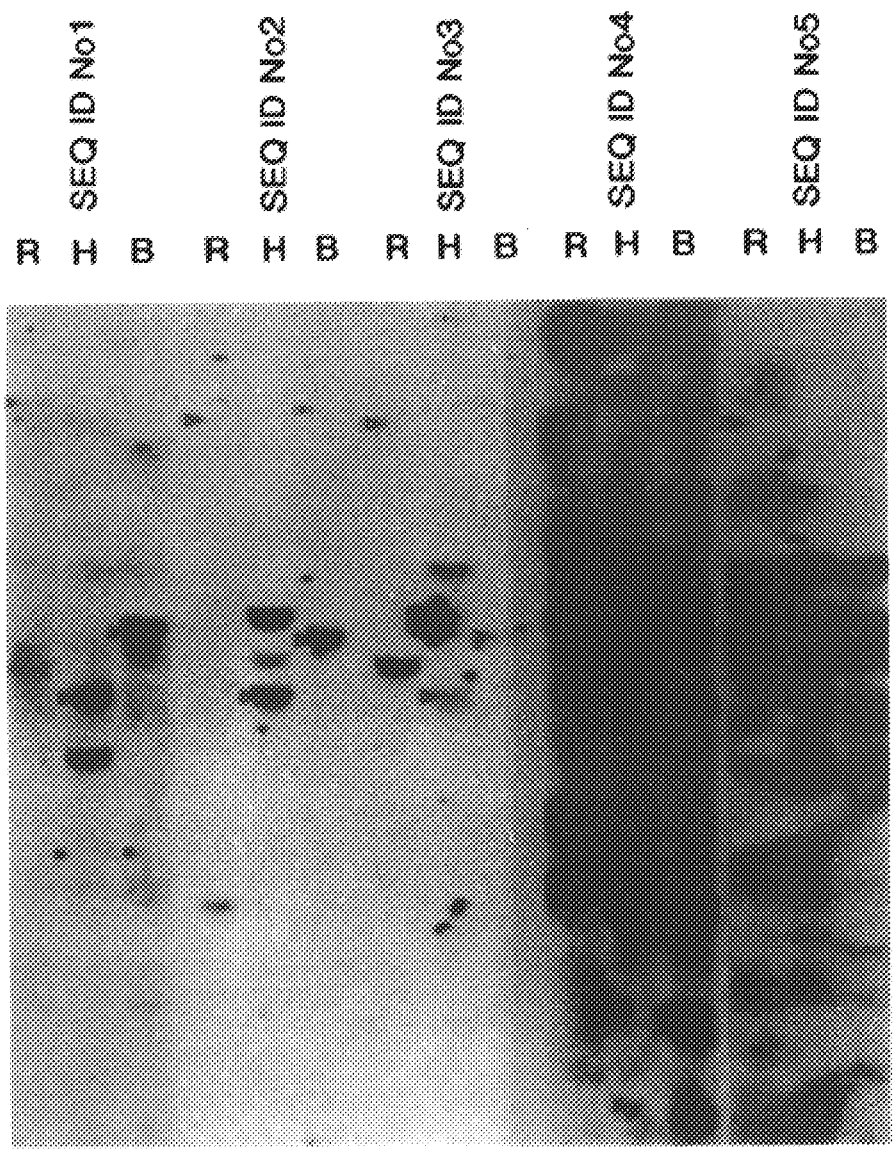

United States Patent [19]
Hercend et al.

[11] Patent Number: 5,817,511
[45] Date of Patent: Oct. 6, 1998

[54] NUCLEOTIDE SEQUENCE CODING FOR VARIABLE REGIONS OF THE α CHAINS OF HUMAN T LYMPHOCYTE RECEPTORS, CORRESPONDING PEPTIDE SEGMENTS AND THE DIAGNOSTIC AND THERAPEUTIC USES

[75] Inventors: Thierry Hercend, Nogent-sur Marne; Frederic Triebel, Seine; Sergio Roman-Roman; Laurent Ferradini, both of Paris, all of France

[73] Assignee: Roussel Uclaf, France

[21] Appl. No.: 348,572

[22] Filed: Apr. 19, 1995

Related U.S. Application Data

[63] Continuation of Ser. No. 934,529, filed as PCT/FR92/00111 Feb. 7, 1992, abandoned.

[30] Foreign Application Priority Data

Feb. 8, 1991 [FR] France ................................. 91 01487
Apr. 12, 1991 [FR] France ................................. 91 04527

[51] Int. Cl.⁶ ............................. C12N 15/12; C07K 7/08; C07K 14/725
[52] U.S. Cl. ..................... 435/320.1; 536/23.5; 530/324; 530/326
[58] Field of Search .................. 536/23.5; 435/69.1, 435/240.2, 252.3, 320.1, 325; 530/324, 326; 514/12

[56] References Cited

PUBLICATIONS

Calman et al. Locus: HUMTCRAR2, Definition: Human T–cell Receptor Alpha J. Region mRNA, Accession: M28593, 1986.

Ayala et al. (1980) Modern Genetics, p. 45, Benjamin/Cummings Pub. Co.

Kimura et al. (1987) Eur. J. Immunol. 17, 375–383.

Leiden et al. (1986) Immuno Genetics 24, 17–23.

Vanden Bark et al. (1989) Nature 341, 541–544.

Chien et al (1993) Immunology Today 14, 597–602.

Goverman et al. (1991) Basic and Clinical Immunology, pp. 73–77, Appleton and Lange.

Baer (1988) Genbank, Locus Humtcazi, Accession #M35617, X07877.

Russo (1989) Genbank, Locus HUMT1414TR, Accession #M23431.

Kinura (1987) Genbank, Locus HUMTCRALJ, Acession #M27377.

Calman (1986) Genbank, Locus HUMTCRAR3, Acession #M28594.

Yoshikai (1986) Genbank, Locus HSTCRA18, Acession #X04953, M13729.

*Primary Examiner*—Stephen Walsh
*Assistant Examiner*—Karen E. Brown
*Attorney, Agent, or Firm*—Bierman, Muserlian and Lucas

[57] ABSTRACT

The present invention relates to new nucleotide sequences coding for variable regions of the α chains of human T lymphocyte receptors, corresponding peptide segments and the diagnostic and therapeutic uses.

6 Claims, 5 Drawing Sheets

Vα1

| | | |
|---|---|---|
| IGRa08 | AGTGTTTCCCTTGCTCAGCCAATGCTCCTGGAGCTTATCCACTGCTGGGGATACATTTTGTCCTGAGAACTGCCAGAGCCCAGTCAGTGACCCAGCCTGA | |
| IGRa08 | CATCCACATCACTGTCTCTGAAGGAGCCTCACTGGAGTTGAGATGTAACTATTCCTATGGGCAACACCTTATCTCTTCTGGTATGTCCAGTCCCCGGC | |
| IGRa08 | CAAGGCCTCCAGCTGCTCCTGAAGTACTTTCAGGAGACACTCTGGTTCAAGGCTGAATTTAAGAGGAGTCAATCTTCCTTCA | |
| IGRa08<br>AE11 | ACCTGAGGAAACCCTCTGTGCATTGGAGTGATGCTGCTGAGTACTTCTGTGCT<br>..T............................................. | 333<br>102 |

FIG. 1A

Vα2

| | | |
|---|---|---|
| IGRa09 | AAATCCCTTGAGAGTTTTACTAGTGATCCTGTGGCTTCAGCTGAGCCGGGTTTGGAGCCAACAGAAGGAGGTGGAGCA | |
| IGRa09<br>AF110 | GAATTCTGGACCCCTCAGTGTTCCAGAGGGAGCCATTGCCTCTCTCAACTGCACTTACAGTGACCGAGGTTCCCAGTCACTGACGAGTTCCTTCTTCTTCTGGTACAGACAATAT<br>................................................................................................................. | |
| IGRa09<br>AF110 | TCTGGGAAAAGCCCTGAGTTGATAATGTCCATATACTCCAATGGTGACAAAGAAGATGAAGGTTTACAGCACAGCTCAATAAAGCCAGTATGTTT<br>.................................................................................................. | |
| IGRa09<br>AF110 | CTCTGCTCATCAGAGACTCCCAGCCCAGTGATTCAGCCACCTACCCTCTGTGCC<br>..................................................... | 330<br>252 |

FIG. 1B

Vα5

| | |
|---|---|
| IGRa10 | GGCCACATTTGGGGAGAGACGAAATGGAGTCATCCCTGGGAGGTGTTTGCTGATTTGTGGCTTCAAGTGGACTGGGTGAAGAGCCAAAAGATAGAACAGAA |
| IGRa10 HAP35 | TTCCGAGGCCCTGAACATTCAGGAGGGTAAAACGGCCACCCTGACCTGCAACTATACAAACTATTCTCCAGCATACTTACAGTGGTACCGACAAGATCCA |
| IGRa10 HAP35 | GGAAGAGGGCCCTGTTTTCTTGCTACTCATACGTGAAAATGAAAAGAAAAGGAAAAGAAGACTGAAGGTCACCTTTGATACCACCCTTAAACAGAGTT |
| IGRa10 HAP35 | TGTTTCATATCACAGCCTCCCAGCCTGCAGACTCAGCTACTACCTCTGTGCT   333 / 249 |

FIG. 1C

Vα7

| | |
|---|---|
| IGRa11 HAP12 | CTCGTGGTATCCTGCAGCAGAATGTGGGGAGTTTTCCTTCTTTATGTTTCCATGAAGATGGGAGGCACTACAGGACAAAACATTGACCAGCCCACTGAGAT |
| IGRa11 HAP12 | GACAGCTACGGAAGGTGCCATTGTCCAGATCAACTGCAGCTACCAGACATCTGGGTTCAACGGGCTGTTCTGGTACCAGCAACATGCTGGGCGAAGCACCC |
| IGRa11 HAP12 | ACATTTCTGTCTTACAATGTTCTGGATGGTTGGAGGAGAAAGGTCGTTTTCTTCATTCCTTAGTCGGTCTAAAGGGTACAGTTACCTCCTTTTGAAGG |
| IGRa11 HAP12 | AGCTCCAGATGAAAGACTCTGCCCTCTTACCTCTGTGCT   318 / 222 |

FIG. 1D

```
Vα22      ATTTGGGTAACACACTAAAGATGAACTATTCTCTCCAGGCTTAGTATCTCTTACTGCTTGGAAGAACCCGTGGAGATTCAGTGACCCAGATGGA
IGRa12

IGRa12    AGGGCCAGTGACTCTCTCAGAAGAGGCCTTCCTGACTATAAACTGCACGTACACAGGATACCCTTCCCTTTCTGGTATGTCCAATATCCTGGA

IGRa12    GAAGGTCTACAGCTCCTCCTGAAAGCCACGAAGGGAAGCAACAAAGGTTTTGAAGCCACATACGTAAAGAAACCACTTCTTTTCCACT
AC9

IGRa12    TGGAGAAAGGCTCAGTTCAAGTGTCAGACTCAGCGGGTGTACTTCTGTGCT    330
AC9                                                          113
```

FIG. 1E

```
            F  G  G  T
IGRJa01G   GGTTATTGCAATAGCACTAAAGACTGTGTAACACCAATGCAGGCAAATCAACCTTTGGGGATGGGACTACGCTCACTGTGAAGCCA
IGRJa02G   GGTTTTTGTAAAGAATGAGCCATTGTGGATAGGCTTTGGGGATGTGCTGCATTGCCGGCCACTCAAGTGATTGTTTTACCA
IGRJa04                                                      TAGATACTGGAGGCTTCAAAACTATCTTTGGAGCAGGAACAAGACTATTTGTTAAAGCA
IGRJa05                                                        CCTAACTGGGGCAAACAACGTCTTCTCTTTGGAGACTGGAACGAGACTCACCGTTCTCCC
IGRJa06                                                           ATGGAGGAAGCCAAGGAAATCTCATCTCTTGGAAGAGGCACTAAACTCTGAGTGTTAACCA
IGRJa07                                                               GGAGCCAATAGTAAGCTGACATTTGGAAGAGGAACACCTGAGTGTTAGACCA
IGRJa08                                                            CTGGTGGCTACAATAAGCTGATTTTTGGAGCAGGAACAAGGCAGGAGCAGCAGCCCCA
IGRJa09                                                                   TGGAAACAAGCTGGTCTTTTGGCGCGAGGAACCATTCTGAGAGTCAAGTCC
```

FIG. 2

NUCLEOTIDE SEQUENCE CODING FOR VARIABLE REGIONS OF THE α CHAINS OF HUMAN T LYMPHOCYTE RECEPTORS, CORRESPONDING PEPTIDE SEGMENTS AND THE DIAGNOSTIC AND THERAPEUTIC USES

This application is a continuation of Ser. No. 07/934,529, filed 24 Nov. 1992, now abandoned, which is a 371 of PCT/FR92/00111, filed 7 Feb. 1992.

The present invention relates to new nucleotide sequences coding for variable regions of α chain T-cell receptors, corresponding peptide segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and γ loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). The known Vα genetic segments have also been classified into 22 subfamilies, 14 of which have only one member (see Concannon et al. (7), Kimura et al. (8), Wilson et al. (9)).

Moreover, about 60 J genetic segments have been described (9).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-a-vis rheumatoid arthritis.

The use of synthetic peptides corresponding to the variable regions of the α or β chains in the treatment of auto-immune diseases is also described (23 and 24).

It is also known that variations exist from one individual to another in the expression of different variable segments of the T-cell receptor in man (27 and 28).

The present inventions aims to enrich the directory of genetic segments coding for the variable regions of the chains of T-cell receptors by providing on the one hand new Vα genetic segments belonging to new subfamilies or belonging to subfamilies of which at least one member is already known, and on the other hand, new Jα genetic segments.

Therefore a subject of the present invention is nucleotide sequences coding for the variable regions of α chains of human T lymphocyte receptors, corresponding to cDNA's containing nucleotide sequences chosen from any one of the following:

a—Vα segments corresponding to one of the sequences SEQ ID No. 1 to 11, and b—Jα segments corresponding to one of the sequences SEQ ID No. 12, 13 and 15 to 20, and the sequences which differ from them by one or more nucleotides.

More particularly a subject of the present invention is:

sequences coding for the variable regions of α chains of human T lymphocyte receptors, corresponding to cDNAs containing nucleotide sequences chosen from any one of the Vα segments corresponding to one of the sequences SEQ ID No. 1 to 10 and the sequences which differ from them by one or more nucleotides, sequences coding for the variable regions of α chains of human T lymphocyte receptors, corresponding to cDNAs containing nucleotide sequences chosen from any one of the Jα segments corresponding to one of the sequences SEQ ID No. 12, 13 and 15 to 20 and the sequences which differ from them by one or more nucleotides.

The expression "and sequences which differ from them by one or more nucleotides", encompasses alleles which differ by up to 8 nucleotides, but more often differ by 1 or 2 nucleotides or which can differ by the deletion or addition of one or two codons.

Also a more particular subject of the invention is:

nucleotide sequences coding for the variable regions of α chains of human T lymphocyte receptors, corresponding to cDNAs corresponding to all or part of the nucleotide sequences chosen from any one of the Vα segments corresponding to one of the sequences SEQ ID No. 2 to 5, and the sequences which differ from them by one or two nucleotides, nucleotide sequences coding for the variable regions of the α chains of human T lymphocyte receptors, corresponding to cDNAs corresponding to all or part of the nucleotide sequences chosen from any one of the Vα segments corresponding to one of the sequences 1 to 200 of SEQ ID No. 1

1 to 467 of SEQ ID No. 6

1 to 77 of SEQ ID No. 7

1 to 151 of SEQ ID No. 8

291 to 386 of SEQ ID No. 9

1 to 260 of SEQ ID No. 10 and the sequences which differ from them by one or two nucleotides, nucleotide sequences coding for the variable regions of the α chains of human T lymphocyte receptors, corresponding to cDNAs corresponding to all or part of the nucleotide sequence corresponding to SEQ ID No. 11 and which contain the 108 nucleotide, nucleotide sequences coding for the variable regions of the α chains of human T lymphocyte receptors, corresponding to cDNAs corresponding to all or part of the nucleotide sequences chosen from any one of the Jα segments corresponding to one of the sequences SEQ ID No. 12, 13 and 15 to 20 and the sequences which differ from them by one or two nucleotides.

By the expression "nucleotide sequences corresponding to cDNAs corresponding to all or part of the nucleotide sequences" is also designated the complete sequences as well as fragments of these sequences including short fragments (oligonucleotides) which can be used as probes (generally containing at least 10 nucleotides) or as primers (generally containing at least 15 nucleotides). In a general fashion, the invention encompasses the group of new oligonucleotides which are fragments of Vα and Jα sequences according to the invention.

As to the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

Also a subject of the present invention is the peptides constituted by or composed of a peptide sequence coded by all or part of the sequence 108 to 364 of SEQ ID No. 11.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (25). The present invention encompasses the peptides resulting from this phenomenon.

The nucleotide sequences according to the invention have been obtained according to the following stages:
  isolation of the RNA's of peripheral lymphocytes of an individual;
  obtaining the complementary DNA using reverse transcriptase and a primer A which is specific to the Cα region (SEQ ID No. 21);
  genetic amplification (by Anchored Polymerase Chain Reaction or A-PCR) using a DNA polymerase, a poly C primer (SEQ ID No. 22) and a primer B which is specific to the Cα region (SEQ ID No. 23);
  a new amplification by A-PCR using DNA polymerase and a primer C which is specific to the Cα region (SEQ ID No. 24);
  insertion in a plasmid vector;
  transformation of a bacterial host with the recombinant vector;
  screening of recombinant bacterial colonies with a labelled oligonucleotide D which is specific to Cα (SEQ ID No. 25);
  extraction of plasmids from positive colonies;
  and sequencing of DNA fragments containing the Cα region.

The present invention can be reproduced, in particular, by bispecific genetic amplification (polymerase chain reaction or PCR) by starting with the peripheral lymphocytes which express the mRNA including the variable or junctional segments corresponding to sequences ID No. 1 to 13 and 15 to 20 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies directed, against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanic anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the F(ab')$_2$ fragments which can be obtained by the enzymatic cleavage of antibody molecules with pepsin, the Fab' fragments which can be obtained by reduction of the disulphide bridges of F(ab')$_2$ fragments and the Fab fragments which can be obtained by the enzymatic cleavage of antibody molecules with papain in the presence of a reducing agent. These fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the field of diagnostics

The oligonucleotides contained in the nucleotide sequences according to the invention can be used to constitute detection probes (generally at least 10 nucleotides) which are capable of hybridizing with a variable region of the α chain or primers for the amplification of DNA (generally containing at least 15 nucleotides and preferably at least 17 nucleotides) which are capable of being linked to a sequence to be amplified.

Thus the oligonucleotides are used in the diagnosis of immune disorders by detecting the presence of nucleic acid sequences which are homologues of a gene coding for the variable regions of α chains of T-cell receptors in the mRNA of a sample from a patient. Different methods can be used to establish a connection between the expression of T-cell genes and an illness. These methods include:
  a—the production and analysis of cDNA expression libraries obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers are used in PCR reactions in a method such as that defined in c above.

The monoclonal antibodies, the fragments or the derivatives of these antibodies according to the invention, in particular the anti Vα antibodies, can be used to study T-type immune responses, for example in the field of the autoimmune diseases of oncology, of allergies, of transplants and of infectious diseases. In particular, the directory of different variable α segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the therapeutic field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (26). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vα or Jα genetic segment is to abolish (or strongly diminish) the expression of a T receptor containing this Vα or Jα segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the T lymphocytes of these oligonucleotides.

The monoclonal antibodies according to the invention, in particular the anti Vα antibodies can be used to modulate the immune system. It is in this way that the antibodies can be administered to block the interaction of the effector T-cells with their specific antigen. Anti T receptor antibodies linked for example to a cytotoxic molecule or a radio-isotope can also be administered in a way so as to obtain a clonal deletion, thanks to the specific fixation on an α chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticulo-endothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the α sub-family specific to the T-cell receptors.

Moreover, as the response of T-cells is often oligoclonal, it is generally convenient to use "cocktails" of several antibodies in therapeutics.

In addition anti Vα antibodies can be used to select T lymphocytes in vitro, for example by passing through a column containing spheres carrying the antibody. This separation of certain T lymphocytes can be used with a view to culturing these lymphocytes before reinfection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or these fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

The present invention will be described in greater detail hereafter by referring to the annexed figures in which:

FIGS. 1A to E show in a line both a known V sequence and a partial sequence of an extension according to the invention for the respective sequences SEQ ID No. 6 to 10, marked IGRa 08 to IGRa 12. In these figures, the numbering of nucleotides starts at the ATG initiation codon (which is underlined). The dots indicate identical nucleotides. The sequences which are assumed to be the leader sequences have a line over them.

FIG. 2 shows in a line the new Jα sequences (SEQ ID No. 12, 13 and 15 to 20) marked IGRJa 01, 02 and 04 to 09. In these sequences the recombination signals of the germinal line are underlined. The amino acids corresponding to highly preserved codons are marked above the sequences. The codons corresponding to a substitution in one position of a preserved amino acid are underlined twice.

FIG. 3 shows the Southern blot analyses of the genomic DNA treated with a restriction enzyme using probes specific to sequences SEQ ID No. 1 to 5. The restriction enzymes used are EcoRI (column R), Hind III (column H) and Bam III (column B). On this figure the triangles mark the position of DNA fragments hybridizing in a specific fashion with Cα.

Figure 4:
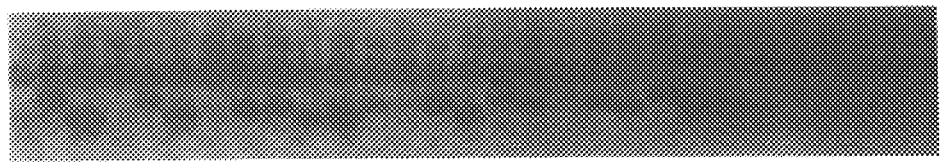

FIG. 4 represents the detection by autoradiography of amplified transcripts of TCRα chains expressed by the peripheral lymphocytes of a healthy individual and of a co-amplified β-actin control.

I—Obtaining the cDNA and amplification by PCR

The peripheral lymphocytes of an individual are used as the DNA source. The total RNA was prepared according to the method using guanidinium isothiocyanate and caesium chloride (Chirgwin (10)) or according to a one-stage method by extraction with guanidinium isothiocyanate, phenol and chloroform (Chomcyznski (11)).

The first cDNA strand was synthesized in a final volume of 50 microliters at a temperature of 42° C. for 1 hour using 5 micrograms of total RNA, reverse transcriptase and a primer A which is specific to the Cα region constituted by the sequence 5'-GTTGCTCCAGGCCACAGCACTG (SEQ ID No. 21). This material was then purified by extraction with phenol/chloroform and precipitation with ammonium acetate. After selecting a 0.45/1 kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C., for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (12)) in a final volume of 100 microliters containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGCCGCGGAGG-14C) (SEQ ID No.22) described by Loh et al. (13) as well as a primer B specific to the Cα region (5'-GTCCATAGACCTCATGTCCAGCACAG) (SEQ ID No. 23).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and 1/10 of this material is purified as a function of size on a 1% low melting point agarose gel.

A second amplification phase is then carried out directly on approximately 10% of the band containing the agarose following the same conditions as previously, except that the primer 5'-ATACACATCAGAATTCTTACTTTG (SEQ ID No. 24) is used as primer C which is specific to the Cα region. The reaction mixture is then precipitated with ethanol and resuspended in 60 µl of $H_2O$.

II—Cloning and sequencing of cDNA's

⅓ of the product of the second amplification is digested with Sac II, separated on 1% agarose gel and purified by absorption on glass beads. The material is inserted in the Bluescript $SK^+$ vector (Stratagene, La Jolla, U.S.A.) and the recombinants obtained are used to transform the XL1-blue strains of E. Coli (Stratagene). After sedimentation in the presence of X-gal and IPTG, a test is carried out on the white colonies using a "dot blot" technique and a third oligonucleotide specific to the Cα region (5'-GTCACTGGATTTAGAGTCT) (SEQ ID No. 25) labelled with $^{32}P$ is used as a probe. The plasmid DNA of positive colonies is extracted and sequencing takes place under the two strands by the process of termination of the dideoxy chain (Sanger et al. (14)) with Sequenase 2.0 (United States Biochemicals, Cleveland, U.S.A.) following the supplier's recommendations. With the exception of the Sequence SEQ ID No. 5, all the nucleotide sequences were determined on the two strands using at least two distinct clones of cDNA.

The sequences obtained were compared with published Vα and Jα sequences using the method developed by Lipman and Pearson (15). The presumed start codons were identified by searching for the presence of the Kozak consensus sequence for the initiation sites of translations in the eukaryotic cells (Kozak (16)). The presence of hydrophobic leader sequences of the N-terminal side was detected by analysis of the hydrophobicity according to the method described by Kyte (17).

III—Southern blot analysis

The DNA was extracted from the human erythroleucemic cell line K562 and digested with one of the following restriction enzymes: EcoR I, BamH I or Hind III. The DNA (15 micrograms) was subjected to electrophoresis on 0.7% agarose and transferred onto Nylon membranes as described by Triebel et al. (18). The hybridizations were carried out at 65° C. with 6×SSC, 0.5% of SDS, 5×Denhardt's and 100 micrograms of denatured salmon sperm DNA for 16 hours. The membranes were washed at 65° C. with 2×SSC, 0.2% of SDS.

β As Vα specific probes, are used the probes obtained by amplification of V-J-C cDNA (>500 bp) containing Vα fragments corresponding to sequences SEQ ID No. 1 to 5 using as a primer the poly-C primer and the C primer. The probes were purified on 1% agarose gel. DNA probes labelled with $^{32}P$ were prepared from fragments purified on agarose by the Feinberg method (19).

IV—Results

By using the A-PCR method, 308 cDNA which hybridize with the Cα clone were cloned, then sequenced. Among these, 172 cDNA correspond to the V-J-Cα variable regions only.

The Vα and Jα sequences of the invention are shown in the list of sequences under SEQ ID No. 1 to 11 and SEQ ID No. 12, 13 and 15 to 20 respectively. The sequences SEQ ID No. 2 to 5 correspond to the new sub-families (designated Vα 25, Vα 26, Vα 27 and Vα 29 respectively) while the sequences SEQ ID No. 1 and 6 to 11 correspond to extensions of known V segments.

1. Vα sequences corresponding to new sub-families

The Southern blot analyses of germinal line DNA subjected to digestion by endonucleases, using V-J-C-α probes containing Vα fragments corresponding to sequences SEQ ID No. 2 to 5 were carried out in "low stringency" hybridization conditions to identify the number of Vα genetic segments belonging to each family and to characterize the DNA restriction fragments carrying these Vα genetic segments. The representative results are shown in FIG. 3.

These analyses show that the sub-family corresponding to the sequence SEQ ID No. 3 includes at least two genetic segments while the other sequences (SEQ ID No. 2, No. 4 and No. 5) probably correspond to unique members.

The sizes of the germinal DNA restriction fragments are as follows:

SEQ ID No. 2: EcoR I 2.2 kb, Hind III 4.8 and 5.7 kb, BamH I 25 kb

SEQ ID No. 3: EcoR I 4.6 and 7.5 kb, Hind III 4.2 and 6.4 kb, BamH I 23 and 4.5 kb SEQ ID No. 4: EcoR I 7.6 kb, Hind III 18 kb, BamH I 9 and 0.9 kb SEQ ID No. 5: EcoR I 5.9 and 4.8 kb, Hind III 6.6 kb, BamH I 6.5 kb.

2. Sequences corresponding to extensions of known V sequences

SEQ ID No. 1 (IGR a 02) corresponds to an extension of the 5' side of the LINV sequence (171 bp) (mengle- Gaw (20)): This sequence defines the sub-family provisionally designated Vα w24.

SEQ ID No. 6 (IGR a 08): this sequence corresponds to an extension of the 5' side of the Vα 1 AE11 clone sequence (Klein et al. (21)). The two straight line sequences are represented in FIG. 1A.

SEQ ID No. 7 (IGR a 09): This sequence corresponds to an extension coding for the NH2 terminal end of the Vα 2 AF110 sequence (Klein already quoted). The two straight line sequences are represented in FIG. 1B. The sequence ID No. 7 corresponds to a consensus sequence. The existence of a T instead of a C is observed in position 206.

SEQ ID No. 8 (IGR a 010): This sequence corresponds to an extension of the 5' region of the Vα HAP35 clone (Yoshikai (22)). The two straight line sequences are represented in FIG 1C. The sequence ID No. 8 corresponds to a consensus sequence. The existence of a G instead of an A in position 307 and the existence of a T instead of a C in position 360 have been observed.

SEQ ID No. 9 (IGR a 11): This sequence corresponds to an extension of the 3' side of the Vα 7 HAP12 sequence (Yoshikai already quoted). The straight line of the sequences is represented in FIG. 1D. The sequence ID No. 9 corresponds to a consensus sequence. The existence of a C instead of a T in position 86 has been observed.

SEQ ID No. 10 (IGR a 12): This sequence includes the complete coding region of a gene of the Vα 22 sub-family which had been previously identified by the partial sequence (113 bp) AC9 (Klein already quoted). The two straight line sequences are represented in FIG. 1E.

SEQ ID No. 11 (IGR a 13): This sequence corresponds in part to the HAVT 32 and HAVT 35 clones (belonging to the Vα 16 (8) sub-family and which have been described as pseudogenes. In fact, following the addition of a nucleotide in position 108, the SEQ ID No. 11 codes for an original variable region of a T lymphocyte receptor. Moreover, this sequence is equivalent to a sequence HSTCAYM (Klein et al. (21)) for the coding part. However, the sequence SEQ No. 11 is the only one which is complete and coding.

3. Jα sequences

The set of new Jα sequences are represented in FIG. 2. Among the 8 Jα segments, the majority of them have a highly preserved amino acid sequence FGXGT of Jα segments as described by Yoshikai already quoted. However, for the IGRJa 07 segment the threonine residue is replaced by an isoleucine residue.

In addition, instead of a phenylalanine residue a cysteine residue is found in IGRJa 02G.

The present invention also aims at providing specific oligonucleotides of different Vα sub-families, which can be used as primers for the amplification of DNA corresponding to these different Vα sub-families, with a view, for example, of a study of the expression of certain Vα (sub-families in a patient and finally of a diagnosis of immune disorders, as indicated above.

The predominant expression of certain Vα sub-families has already been studied using an incomplete range of oligonucleotides. In this way Nitta et al. (29) have described the predominant expression of Vα 7 genes in the lymphocytes infiltrating the tumours. Moreover, Sottini et al. (30) have described the study of the directory of Vα's, in patients suffering from rheumatoid arthritis.

The present invention aims to provide a complete range of oligonucleotides allowing the study, of both known Vα sub-families and new Vα sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of α chains of T-cell receptors, chosen from the sequences SEQ ID No. 26 to 54.

Also a subject of the present invention is the use, as primers for the amplification of DNA corresponding to the variable regions of α chains of T-cell receptors, of oligonucleotides chosen from the sequences SEQ ID No. 26 to 54.

Also a subject of the present invention is a detection process of nucleotide sequences coding for the Vα segments of T receptors or of cDNA corresponding to transcription products of the latter, in a biological sample, characterized in that it includes:

a) the amplification of DNA with at least one pair of primers formed by one of the oligonucleotides chosen from the sequences SEQ ID No. 26 to 54 and one oligonucleotide belonging to segment Cα, and b) the detection of amplified sequences with a Cα probe.

The oligonucleotide belonging to a Cα segment used for the amplification can be, in particular, chosen from the sequences SEQ ID No. 55 and 56.

To check the efficiency of the amplification, the operation is preferably carried out in the presence of a pair of control primers and the corresponding control sequence amplified using a corresponding control probe is detected.

This pair of control primers can correspond to two Cβ segments, for example the CβF and CβK primers corresponding to sequences SEQ ID No. 61 and 62. Then a Cβ detection probe is used (corresponding for example to the sequence SEQ ID No. 63). But this pair of primers can also be constituted by two primers belonging to β-actin, notably those corresponding to sequences SEQ ID No. 58 and 59. Then a detection probe corresponding to a sequence of β-actin, such as the sequence SEQ ID No. 60, is used.

Also a subject of the present invention is a diagnostic kit for the implementation of the process defined previously, which includes:

a) at least one oligonucleotide chosen from the sequences SEQ ID No. 26 to 54, b) a Cβ primer, c) a Cβ probe.

In addition such a kit advantageously contains:

d) a pair of control primers, e) a control probe.

This kit can contain in particular:

a) the group of 29 oligonucleotides corresponding to sequences SEQ ID No. 26 to 54, b) a Cβ primer chosen from the sequences corresponding to sequences SEQ ID No. 55 and 56, c) a pair of control primers for β-actin having a sequence corresponding to sequences SEQ ID NO. 58 and 59 respectively, d) a Cα probe corresponding to the sequence SEQ ID No. 57, e) a control probe for β-actin corresponding to the sequence SEQ ID No. 60.

In the information given in the list of sequences for the sequences 26 to 60, the sequences SEQ ID No. 26 to 47 correspond to sequences belonging to clones of known Vα 1 to Vα 22 sub-families (available from the EMBL database) or to sequences which differ from them by one or two nucleotides.

The sequences SEQ ID No. 49, 50, 51, 52 and 54 correspond to sequences belonging to clones of new sub-families of the invention, corresponding to sub-families provisionally designated Vα w24, Vα w25, Vα w26, Vα w27 and Vα w29 (w indicating that the designation is pending definitive designation).

The sequences SEQ ID No. 48 and 53 correspond to sequences belonging to clones IGRa01 and IGRa06 respectively of known sub-families but having not yet received definitive designation (Vα w23 and Vα w28 respectively) one member (31) and Bernard O. et al. (32) respectively). The complete sequence of IGRa06 has not yet been published.

The sequences SEQ ID No. 55 and 56 are two examples of oligonucleotides which can be used as Cα primers for amplification.

The sequence SEQ ID No. 57 is the sequence of a C probe which can be used for the detection of amplified DNAs.

The sequences SEQ ID No. 58, 59 and 60 are respectively the sequences of a pair of oligonucleotides belonging to the sequence of β-actin which can be used to check the amplification and the sequence of a probe for detecting the corresponding amplified DNAs.

In the list of sequences the position indicated is the position of the 5' end counting from the predicted initiation site of the ATG translation. In the case where the sequences are incomplete (unknown 5' region), the position (marked with an asterisk) is given relative to the first nucleotide of the sequence. Nucleotides that correspond to mismatches introduced relative to the natural sequence in SEQ ID NO:26, SEQ ID NO:27, SEQ ID NO:32, SEQ ID NO:34, SEQ ID NO:40, SEQ ID NO:42, SEQ ID NO:49, SEQ ID NO:50, SEQ ID NO:51, and SEQ ID NO:53 are indicated in the information fields of those sequence listings.

The oligonucleotides were sythesized with an Applied Biosystems 381 A automated DNA synthesizer using the β-cyano-ethylphosphoramidite method (Sinha N. et al. (33)) and following the protocol recommended by the manufacturer. The oligonucleotides were detritylated in the apparatus, cleaved from the support and deprotected with ammonia (at 60° C. for 5 hours). The crude products were purified by reverse phase high pressure chromatography on $\mu$-bondapak C18 column using an acetonitrile gradient (9 to 15%) in a 0.01M triethylammonium acetate buffer at pH 5.5.

The amplification carried out using the primers according to the invention can be, in particular, the technique of amplification by PCR (Polymerase Chain Reaction) as described by Saiki et al. (12) and in U.S. Pat. Nos. 4,683,195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 25 to 40 times.

The probes which are used for detecting the amplified sequences can be obtained by labelling the oligonucleotides with a radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 11). The complementary DNA was synthesized in a final volume of 20 $\mu$l at 42° C. for one hour using 1 to 5 $\mu$g of total RNA, the reverse transcriptase and the CβB primer (1.25 $\mu$M).

The material obtained was then heated at 95° C. for 3 minutes before being subjected to an amplification according to the PCR technique using in parallel each of the specific Vα primers corresponding to sequences SEQ ID No. 26 to 54 and the CαB primer specific to the Cβ region (SEQ ID No. 56). This amplification was carried out in a final volume of 10 $\mu$l per tube containing 50 mM of KCl, 10 mM of tris-HCl pH 8.3, 1.5 mM of $MgCl_2$, 0.1% (weight/volume) of gelatine, 200 $\mu$M of dNTP, 0.25 units of Taq polymerase and 0.25 $\mu$M of each primer. A control amplification was carried out in each tube from 25 mN of a DNA fragment of β-actin of 877 base pairs prepared by PCR and Act 1 and Act 2 primers (SEQ ID No. 58 and 59) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on a 2% agarose gel, transferred onto nylon membranes in an alkaline buffer and hybridized simultaneously with the α C oligonucleotide probes (SEQ ID No. 57) and Act 3 (SEQ ID No. 60) labelled with $^{32}P$ by the polynucleotidyl T4 kinase enzyme. The hybridization was carried out at 42° C. for 16 hours in a buffer containing 6xSSC, 0.5% SDS, 5xDenhardt's, 0.05% $NaH_2PO_4$ and 100 $\mu$/ml of denatured salmon sperm DNA. The membranes were then washed with SSC 6x, 20 mM $NaH_2PO_4$, twice at ambient temperature for 5 minutes and once at 50° C. for 30 minutes then autoradiographed.

The results obtained are shown in FIG. 4.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vα oligonucleotide and the Cα primer.

With the individual tested, FIG. 4 shows the preferential expression of certain genetic segments defined relative to the others. For example, the Vα 27, 28 and 29 sub-families are less well represented than the Vβ 2, 3 and 6 sub-families.

REFERENCES

1. Meuer, S. C., et al., J. Exp. Med. 1983. 157:705.
2. Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Concannon, P., et al., Proc. Natl. Acad. Sci. USA. 1986. 83:6598.
8. Kimura, N., et al., Eur. J. Immunol. 1987. 17:375.
9. Wilson, R. K., et al., Immunological Reviews 1988c. 101:149.
10. Chirgwin, J. M., et al. Biochemistry 1979. 18:5294.

11. Chomczynski, P., et al., Anal. Biochem. 1987. 162:156.
12. Saiki, R. K., et al., Science 1988. 239:487.
13. Loh, E. Y., et al., Science 1989. 243:217.
14. Sanger, F., et al., Proc. Natl. Acad. Sci. USA 1977. 74:5463.
15. Lipman, D. J., et al., Science 1985. 227:1435.
16. Kozak, M., Nucl. Acids Res. 1984. 12:857.
17. Kyte, J., et al., R. F., J. Mol. Biol. 1982. 157:105.
18. Triebel, F., et al., J. Immun. 1988. 140:300.
19. Feinberg, A. P., et al., Anal. Bichem. 1983. 132:6.
20. Mengle-Gaw, L., et al., The EMBO Journal, 1987. 6:2273.
21. Klein, M. H., et al., Proc. Natl. Acad. Sci. USA 1987. 84:6884.
22. Yoshikai, Y., et al., J. Exp. Med. 1986. 164:90.
23. Wandenbirk, A., et al., Nature, 341, 541.
24. Janeway, C., Nature, 341, 482.
25. Li, Y., J. Exp. Med., 171, 221.
26. Acha-Orbea, H., EMBO Journal, 1990, 9, 12, 3815.
27. Kappler, J., Science 244, 811.
28. Choi, Y., PNAS, 86, 8941.
29. Nitta T. et al., Science 1990, 249, 672.
30. Sottini A. et al., Eur. J. Immunol., 1991, 21, 461.
31. Hinkkanen A. et al., Immunogenetics, 1989, 29, 131.
32. Bernard O. et al., Oncogene, 1988, 2, 195.
33. Sinha N. et al., Nucleic Acids Res. 1984, 12, 4539.

We claim:

1. An isolated nucleic acid coding for a variable region of an α chain of human T lymphocyte receptor, said nucleic acid consisting of a nucleotide sequence chosen from any one of the
   nucleotide sequences of SEQ. ID. NOS:1 to 3, 5, 7, 9 to 11, 13 and 15 to 19.

2. An isolated nucleic acid of claim 1 chosen from any one of the nucleotide sequences of
   1 to 200 of SEQ ID No. 1,
   1 to 77 of SEQ ID No. 7,
   1 to 151 of SEQ ID No. 8,
   291 to 386 of SEQ ID No. 9 and
   1 to 260 of SEQ ID No. 10.

3. An isolated nucleic acid coding for a variable region of an α chain of human T lymphocyte receptor, said nucleic acid consisting of a nucleotide sequence chosen from any of the nucleotide sequences of SEQ ID Nos:1 to 3, 5, 7, 9 and 10.

4. An isolated nucleic acid coding for a variable region of an α chain of human T lymphocyte receptor, said nucleic acid consisting of a nucleotide sequence chosen from any one of the nucleotide sequences of SEQ ID. Nos. 13 and 15 to 20.

5. A peptide encoded by a nucleotide sequence selected from the group consisting of:
   nucleotides 36 to 400 of SEQ ID NO:1,
   nucleotides 77 to 400 of SEQ ID NO:2,
   nucleotides 10 to 339 of SEQ ID NO:3,
   nucleotides 32 to 361 of SEQ ID NO:5,
   nucleotides 1 to 330 of SEQ ID NO:7,
   nucleotides 69 to 386 of SEQ ID NO:9,
   nucleotides 54 to 383 of SEQ ID NO:10,
   nucleotides 32 to 364 of SEQ ID NO:11,
   nucleotides 221 to 277 of SEQ ID NO:13,
   nucleotides 3 to 59 of SEQ ID NO:15,
   nucleotides 2 to 58 of SEQ ID NO:16,
   nucleotides 3 to 59 of SEQ ID NO:17,
   nucleotides 1 to 54 of SEQ ID NO:18 and
   nucleotides 3 to 56 of SEQ ID NO:19.

6. An expression vector containing a nucleic acid coding for one of the peptides as defined in claim 5.

* * * * *

UNITED STATES PATENT AND TRADEMARK OFFICE
CERTIFICATE OF CORRECTION

PATENT NO. : 5,817,511
DATED     : October 6, 1998
INVENTOR(S) : T. HERCEND et al It is certified that error appears in the above-indentified patent and that said Letters Patent is hereby corrected as shown below:

Column 61, line 55, delete "1 to 151 of SEQ ID NO. 8,"

Signed and Sealed this

Sixth Day of April, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 62

( 2 ) INFORMATION FOR SEQ ID NO: 1:

( i ) SEQUENCE CHARACTERISTICS:
        ( A ) LENGTH: 371
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a O2
        ( B ) LOCATION:
        ( C ) IDENTIFICATION METHOD:
        ( D ) OTHER INFORMATION: SEQUENCE V Alpha w24

( x i ) SEQUENCE DESCRIPTION: SEQ ID NO:1:

```
                AGTCAACTTC  TGGGAGCAGT  CTCTGCAGAA  TAAAA  ATG  AAA  AAG  CAT              47
                                                          Met  Lys  Lys  His
                                                          1

CTG  ACG  ACC  TTC  TTG  GTG  ATT  TTG  TGG  CTT  TAT  TTT  TAT  AGG  GGG  AAT              95
Leu  Thr  Thr  Phe  Leu  Val  Ile  Leu  Trp  Leu  Tyr  Phe  Tyr  Arg  Gly  Asn
5                       10                      15                      20

GGC  AAA  AAC  CAA  GTG  GAG  CAG  AGT  CCT  CAG  TCC  CTG  ATC  ATC  CTG  GAG             143
Gly  Lys  Asn  Gln  Val  Glu  Gln  Ser  Pro  Gln  Ser  Leu  Ile  Ile  Leu  Glu
                    25                      30                      35

GGA  AAG  AAC  TGC  ACT  CTT  CAA  TGC  AAT  TAT  ACA  GTG  AGC  CCC  TTC  AGC             191
Gly  Lys  Asn  Cys  Thr  Leu  Gln  Cys  Asn  Tyr  Thr  Val  Ser  Pro  Phe  Ser
               40                      45                      50

AAC  TTA  AGG  TGG  TAT  AAG  CAA  GAT  ACT  GGG  AGA  GGT  CCT  GTT  TCC  CTG             239
Asn  Leu  Arg  Trp  Tyr  Lys  Gln  Asp  Thr  Gly  Arg  Gly  Pro  Val  Ser  Leu
          55                      60                      65

ACA  ATC  ATG  ACT  TTC  AGT  GAG  AAC  ACA  AAG  TCG  AAC  GGA  AGA  TAT  ACA             287
Thr  Ile  Met  Thr  Phe  Ser  Glu  Asn  Thr  Lys  Ser  Asn  Gly  Arg  Tyr  Thr
     70                      75                      80

GCA  ACT  CTG  GAT  GCA  GAC  ACA  AAG  CAA  AGC  TCT  CTG  CAC  ATC  ACA  GCC             335
```

| Ala | Thr | Leu | Asp | Ala | Asp | Thr | Lys | Gln | Ser | Ser | Leu | His | Ile | Thr | Ala |
| --- | --- | --- | --- | --- | --- | --- | --- | --- | --- | --- | --- | --- | --- | --- | --- |
| 85 | | | | 90 | | | | | 95 | | | | | | 100 |

| TCC | CAG | CTC | AGC | GAT | TCA | GCC | TCC | TAC | ATC | TGT | GTG | | | | | 371 |
|---|---|---|---|---|---|---|---|---|---|---|---|---|---|---|---|---|
| Ser | Gln | Leu | Ser | Asp | Ser | Ala | Ser | Tyr | Ile | Cys | Val | | | | | |
| | | | | 105 | | | | 110 | | | | | | | | |

(2) INFORMATION FOR SEQ ID NO: 2:

(i) SEQUENCE CHARACTERISTICS:
        (A) LENGTH: 400
        (B) TYPE: NUCLEOTIDE
        (C) STRANDEDNESS: DOUBLE
        (D) TOPOLOGY: LINEAR (ii) MOLECULE TYPE: cDNA TO mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 03
        (B) LOCATION:
        (C) IDENTIFICATION METHOD:
        (D) OTHER INFORMATION: SEQUENCE V Alpha w 25

(xi) SEQUENCE DESCRIPTION: SEQ ID NO:2:

| | | | | GACTCTAAGC | CCAAGAGAGT | TTCTTGAAGC | AAAAAAAAAA | 40 |
|---|---|---|---|---|---|---|---|---|

| AAAACCCATT | CAGGAAATAA | TTCTTTGCTG | ATAAGG | ATG | CTC | CTT | GAA | CAT | TTA | 94 |
|---|---|---|---|---|---|---|---|---|---|---|
| | | | | Met | Leu | Leu | Glu | His | Leu | |
| | | | | 1 | | | | 5 | | |

| TTA | ATA | ATC | TTG | TGG | ATG | CAG | CTG | ACA | TGG | GTC | AGT | GGT | CAA | CAG | CTG | 142 |
|---|---|---|---|---|---|---|---|---|---|---|---|---|---|---|---|---|
| Leu | Ile | Ile | Leu | Trp | Met | Gln | Leu | Thr | Trp | Val | Ser | Gly | Gln | Gln | Leu | |
| | | 10 | | | | | | 15 | | | | | 20 | | | |

| AAT | CAG | AGT | CCT | CAA | TCT | ATG | TTT | ATC | CAG | GAA | GGA | GAA | GAT | GTC | TCC | 190 |
|---|---|---|---|---|---|---|---|---|---|---|---|---|---|---|---|---|
| Asn | Gln | Ser | Pro | Gln | Ser | Met | Phe | Ile | Gln | Glu | Gly | Glu | Asp | Val | Ser | |
| | | 25 | | | | | 30 | | | | | 35 | | | | |

| ATG | AAC | TGC | ACT | TCT | TCA | AGC | ATA | TTT | AAC | ACC | TGG | CTA | TGG | TAC | AAG | 238 |
|---|---|---|---|---|---|---|---|---|---|---|---|---|---|---|---|---|
| Met | Asn | Cys | Thr | Ser | Ser | Ser | Ile | Phe | Asn | Thr | Trp | Leu | Trp | Tyr | Lys | |
| | 40 | | | | 45 | | | | | 50 | | | | | | |

| CAG | GAC | CCT | GGG | GAA | GGT | CCT | GTC | CTC | TTG | ATA | GCC | TTA | TAT | AAG | GCT | 286 |
|---|---|---|---|---|---|---|---|---|---|---|---|---|---|---|---|---|
| Gln | Asp | Pro | Gly | Glu | Gly | Pro | Val | Leu | Leu | Ile | Ala | Leu | Tyr | Lys | Ala | |
| 55 | | | | | 60 | | | | 65 | | | | | 70 | | |

| GGT | GAA | TTG | ACC | TCA | AAT | GGA | AGA | CTG | ACT | GCT | CAG | TTT | GGT | ATA | ACC | 334 |
|---|---|---|---|---|---|---|---|---|---|---|---|---|---|---|---|---|
| Gly | Glu | Leu | Thr | Ser | Asn | Gly | Arg | Leu | Thr | Ala | Gln | Phe | Gly | Ile | Thr | |
| | | | | 75 | | | | | 80 | | | | | 85 | | |

| AGA | AAG | GAC | AGC | TTC | CTG | AAT | ATC | TCA | GCA | TCC | ATA | CCT | AGT | GAT | GTA | 382 |
|---|---|---|---|---|---|---|---|---|---|---|---|---|---|---|---|---|
| Arg | Lys | Asp | Ser | Phe | Leu | Asn | Ile | Ser | Ala | Ser | Ile | Pro | Ser | Asp | Val | |
| | | | 90 | | | | | 95 | | | | | 100 | | | |

| GGC | ATC | TAC | TTC | TGT | GCT | | | | | | | | | | | 400 |
|---|---|---|---|---|---|---|---|---|---|---|---|---|---|---|---|---|
| Gly | Ile | Tyr | Phe | Cys | Ala | | | | | | | | | | | |
| | | 105 | | | | | | | | | | | | | | |

(2) INFORMATION FOR SEQ ID NO: 3:

(i) SEQUENCE CHARACTERISTICS:
        (A) LENGTH: 339
        (B) TYPE: NUCLEOTIDE
        (C) STRANDEDNESS: DOUBLE
        (D) TOPOLOGY: LINEAR

-continued ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: IGR a 04
    ( B ) LOCATION:
    ( C ) IDENTIFICATION METHOD:
    ( D ) OTHER INFORMATION: SEQUENCE V Alpha w26

( x i ) SEQUENCE DESCRIPTION: SEQ ID NO:3:

```
    AGCTAAGGG ATG GAG ACT GTT CTG CAA GTA CTC CTA GGG ATA TTG GGG        48
              Met Glu Thr Val Leu Gln Val Leu Leu Gly Ile Leu Gly
               1               5                   10

TTC CAA GCA GCC TGG GTC AGT AGC CAA GAA CTG GAG CAG AGT CCT CAG        96
Phe Gln Ala Ala Trp Val Ser Ser Gln Glu Leu Glu Gln Ser Pro Gln
     15              20                  25

TCC TTG ATC GTC CAA GAG GGA AAG AAT CTC ACC ATA AAC TGC ACG TCA       144
Ser Leu Ile Val Gln Glu Gly Lys Asn Leu Thr Ile Asn Cys Thr Ser
 30              35                  40                  45

TCA AAG ACG TTA TAT GGC TTA TAC TGG TAT AAG CAA AAG TAT GGT GAA       192
Ser Lys Thr Leu Tyr Gly Leu Tyr Trp Tyr Lys Gln Lys Tyr Gly Glu
             50                  55                  60

GGT CTT ATC TTC TTG ATG ATG CTA CAG AAA GGT GGG GAA GAG AAA AGT       240
Gly Leu Ile Phe Leu Met Met Leu Gln Lys Gly Gly Glu Glu Lys Ser
             65                  70                  75

CAT GAA AAG ATA ACT GCC AAG TTG GAT GAG AAA AAG CAG CAA AGT TCC       288
His Glu Lys Ile Thr Ala Lys Leu Asp Glu Lys Lys Gln Gln Ser Ser
         80                  85                  90

CTG CAT ATC ACA GCC TCC CAG CCC AGC CAT GCA GGC ATC TAC CTC TGT       336
Leu His Ile Thr Ala Ser Gln Pro Ser His Ala Gly Ile Tyr Leu Cys
     95                  100                 105

GGA                                                                   339
Gly
110
```

( 2 ) INFORMATION FOR SEQ ID NO: 4:

( i ) SEQUENCE CHARACTERISTICS:
    ( A ) LENGTH: 335
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: IGR a 05
    ( B ) LOCATION:
    ( C ) IDENTIFICATION METHOD:
    ( D ) OTHER INFORMATION: SEQUENCE V Alpha w27

( x i ) SEQUENCE DESCRIPTION: SEQ ID NO:4:

```
            AGAAAAAAAA AATGAAGAAG CTACTAGCAA TGATCCTGTG GCTTCAACTA           50

GACCGGTTAA GTGGAGAGCT GAAAGTG GAA CAA AAC CCT CTG TTC   95
                                                   Glu Gln Asn Pro Leu Phe
                                                    1                   5

CTG AGC ATG CAG GAG GGA AAA AAC TAT ACC ATC TAC TGC AAT TAT TCA           143
Leu Ser Met Gln Glu Gly Lys Asn Tyr Thr Ile Tyr Cys Asn Tyr Ser
             10                  15                  20

ACC ACT TCA GAC AGA CTG TAT TGG TAC AGG CAG GAT CCT GGG AAA AGT           191
Thr Thr Ser Asp Arg Leu Tyr Trp Tyr Arg Gln Asp Pro Gly Lys Ser
         25                  30                  35

CTG GAA TCT CTG TTT GTG TTG CTA TCA AAT GGA GCA GTG AAG CAG GAG           239
Leu Glu Ser Leu Phe Val Leu Leu Ser Asn Gly Ala Val Lys Gln Glu
     40                  45                  50

GGA CGA TTA ATG GCC TCA CTT GAT ACC AAA GCC CGT CTC AGC ACC CTC           287
Gly Arg Leu Met Ala Ser Leu Asp Thr Lys Ala Arg Leu Ser Thr Leu
 55                  60                  65                  70

CAC ATC ACA GCT GCC GTG CAT GAC CTC TCT GCC ACC TAC TTC TGT GCC           335
His Ile Thr Ala Ala Val His Asp Leu Ser Ala Thr Tyr Phe Cys Ala
                 75                  80                  85
```

( 2 ) INFORMATION FOR SEQ ID NO: 5:

( i ) SEQUENCE CHARACTERISTICS:
        ( A ) LENGTH: 361
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 07
        ( B ) LOCATION:
        ( C ) IDENTIFICATION METHOD:
        ( D ) OTHER INFORMATION: SEQUENCE V Alpha w29

( x i ) SEQUENCE DESCRIPTION: SEQ ID NO:5:

```
            GAAGCTGACT GGATATTCTG GCAGGCAAG G ATG GAG ACT CTC CTG           46
                                              Met Glu Thr Leu Leu
                                               1               5

AAA GTG CCT TCA GGC ACC TTG TTG TGG CAG TTG ACC TGG GTG GGA AGC           94
Lys Val Pro Ser Gly Thr Leu Leu Trp Gln Leu Thr Trp Val Gly Ser
             10                  15                  20

CAA CAA CCA GTG CAG AGT CCT CAA GCC GTG ATC CTC CGA GAA GGG GAA          142
Gln Gln Pro Val Gln Ser Pro Gln Ala Val Ile Leu Arg Glu Gly Glu
         25                  30                  35

GAT GCT GTC ACC AAC TGC AGT TCC TCC AAG GCT TTA TAT TCT GTA CAC          190
Asp Ala Val Thr Asn Cys Ser Ser Ser Lys Ala Leu Tyr Ser Val His
         40                  45                  50

TGG TAC AGG CAG AAG CAT GGT GAA GCA CCC GTC TTC CTG ATG ATA TTA          238
Trp Tyr Arg Gln Lys His Gly Glu Ala Pro Val Phe Leu Met Ile Leu
 55                  60                  65

CTG AAG GGT GGA GAA CAG ATG CGT CGT GAA AAA ATA TCT GCT TCA TTT          286
```

```
Leu  Lys  Gly  Gly  Glu  Gln  Met  Arg  Arg  Glu  Lys  Ile  Ser  Ala  Ser  Phe
70                  75                       80                       85

AAT  GAA  AAA  AAG  CAG  CAA  AGC  TCC  CTG  TAC  CTT  ACG  GCC  TCC  CAG  CTC      334
Asn  Glu  Lys  Lys  Gln  Gln  Ser  Ser  Leu  Tyr  Leu  Thr  Ala  Ser  Gln  Leu
                    90                       95                      100

AGT  TAC  TCA  GGA  ACC  TAC  TTC  TGC  GGG                                          361
Ser  Tyr  Ser  Gly  Thr  Tyr  Phe  Cys  Gly
               105                      110
```

( 2 ) INFORMATION FOR SEQ ID NO: 6:

( i ) SEQUENCE CHARACTERISTICS:
        ( A ) LENGTH: 569
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 08
        ( B ) LOCATION:
        ( C ) IDENTIFICATION METHOD:
        ( D ) OTHER INFORMATION: SEQUENCE V Alpha 1

( x i ) SEQUENCE DESCRIPTION: SEQ ID NO:6:

```
                                                                TCAGTTTCTT       10

CTTCCTGCAG  CTGGTTGAGT  TCTTTCCAGA  CAAAGACAAG  TGACAAGAAT  TAGAGGTTTA            70

AAAAGCAACC  AGATTCATCT  CAGCAGCTTT  TGTAGTTTTA  AATAAGCAAG  GAGTTTCTCC           130

AGCGAAACTT  CCTCACACCT  CTTGGTCTTG  GTCTCTTCAG  ACACTTTCCT  TCCTGTTCTC           190

TGGAGATCTT  GCAGAAAAGA  GCCTGCAGTG  TTTCCCTTGC  TCAGCC ATG  CTC  CTG             245
                                                        Met  Leu  Leu
                                                         1

GAG  CTT  ATC  CCA  CTG  CTG  GGG  ATA  CAT  TTT  GTC  CTG  AGA  ACT  GCC  AGA   293
Glu  Leu  Ile  Pro  Leu  Leu  Gly  Ile  His  Phe  Val  Leu  Arg  Thr  Ala  Arg
          5                        10                       15

GCC  CAG  TCA  GTG  ACC  CAG  CCT  GAC  ATC  CAC  ATC  ACT  GTC  TCT  GAA  GGA   341
Ala  Gln  Ser  Val  Thr  Gln  Pro  Asp  Ile  His  Ile  Thr  Val  Ser  Glu  Gly
20                       25                       30                       35

GCC  TCA  CTG  GAG  TTG  AGA  TGT  AAC  TAT  TCC  TAT  GGG  GCA  ACA  CCT  TAT   389
Ala  Ser  Leu  Glu  Leu  Arg  Cys  Asn  Tyr  Ser  Tyr  Gly  Ala  Thr  Pro  Tyr
               40                       45                       50

CTC  TTC  TGG  TAT  GTC  CAG  TCC  CCC  GGC  CAA  GGC  CTC  CAG  CTG  CTC  CTG   437
Leu  Phe  Trp  Tyr  Val  Gln  Ser  Pro  Gly  Gln  Gly  Leu  Gln  Leu  Leu  Leu
               55                       60                       65

AAG  TAC  TTT  TCA  GGA  GAC  ACT  CTG  GTT  CAA  GGC  ATT  AAA  GGC  TTT  GAG   485
Lys  Tyr  Phe  Ser  Gly  Asp  Thr  Leu  Val  Gln  Gly  Ile  Lys  Gly  Phe  Glu
               70                       75                       80

GCT  GAA  TTT  AAG  AGG  AGT  CAA  TCT  TCC  TTC  AAC  CTG  AGG  AAA  CCC  TCT   533
Ala  Glu  Phe  Lys  Arg  Ser  Gln  Ser  Ser  Phe  Asn  Leu  Arg  Lys  Pro  Ser
85                       90                       95

GTG  CAT  TGG  AGT  GAT  GCT  GCT  GAG  TAC  TTC  TGT  GCT                       569
Val  His  Trp  Ser  Asp  Ala  Ala  Glu  Tyr  Phe  Cys  Ala
100                      105                      110
```

( 2 ) INFORMATION FOR SEQ ID NO: 7:

( i ) SEQUENCE CHARACTERISTICS:
        ( A ) LENGTH: 330
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 09
        ( B ) LOCATION:
        ( C ) IDENTIFICATION METHOD:
        ( D ) OTHER INFORMATION: SEQUENCE V Alpha 2

( x i ) SEQUENCE DESCRIPTION: SEQ ID NO:7:

```
AAA  TCC  TTG  AGA  GTT  TTA  CTA  GTG  ATC  CTG  TGG  CTT  CAG  CTG  AGC  CGG       48
Lys  Ser  Leu  Arg  Val  Leu  Leu  Val  Ile  Leu  Trp  Leu  Gln  Leu  Ser  Arg
 1                    5                        10                       15

GTT  TGG  AGC  CAA  CAG  AAG  GAG  GTG  GAG  CAG  AAT  TCT  GGA  CCC  CTC  AGT       96
Val  Trp  Ser  Gln  Gln  Lys  Glu  Val  Glu  Gln  Asn  Ser  Gly  Pro  Leu  Ser
               20                        25                       30

GTT  CCA  GAG  GGA  GCC  ATT  GCC  TCT  CTC  AAC  TGC  ACT  TAC  AGT  GAC  CGA      144
Val  Pro  Glu  Gly  Ala  Ile  Ala  Ser  Leu  Asn  Cys  Thr  Tyr  Ser  Asp  Arg
          35                        40                       45

GGT  TCC  CAG  TCC  TTC  TTC  TGG  TAC  AGA  CAA  TAT  TCT  GGG  AAA  AGC  CCT      192
Gly  Ser  Gln  Ser  Phe  Phe  Trp  Tyr  Arg  Gln  Tyr  Ser  Gly  Lys  Ser  Pro
     50                        55                       60

GAG  TTG  ATA  ATG  TCC  ATA  TAC  TCC  AAT  GGT  GAC  AAA  GAA  GAT  GGA  AGG      240
Glu  Leu  Ile  Met  Ser  Ile  Tyr  Ser  Asn  Gly  Asp  Lys  Glu  Asp  Gly  Arg
 65                       70                       75                       80

TTT  ACA  GCA  CAG  CTC  AAT  AAA  GCC  AGC  CAG  TAT  GTT  TCT  CTG  CTC  ATC      288
Phe  Thr  Ala  Gln  Leu  Asn  Lys  Ala  Ser  Gln  Tyr  Val  Ser  Leu  Leu  Ile
                    85                       90                       95

AGA  GAC  TCC  CAG  CCC  AGT  GAT  TCA  GCC  ACC  TAC  CTC  TGT  GCC                 330
Arg  Asp  Ser  Gln  Pro  Ser  Asp  Ser  Ala  Thr  Tyr  Leu  Cys  Ala
               100                      105                      110
```

( 2 ) INFORMATION FOR SEQ ID NO: 8:

( i ) SEQUENCE CHARACTERISTICS:
        ( A ) LENGTH: 400
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
  ( A ) NAME/KEY: IGR a 10
  ( B ) LOCATION:
  ( C ) IDENTIFICATION METHOD:
  ( D ) OTHER INFORMATION: SEQUENCE V Alpha 5

( x i ) SEQUENCE DESCRIPTION: SEQ ID NO:8:

```
              GCCAAACAGA   ATGGCTTTTT   GGCTGAGAAG   GCTGGGTCTA   CATTTCAGGC              50

CACATTTGGG   GAGACGA  ATG   GAG   TCA   TCC   CTG   GGA   GGT   GTT   TTG   94
                                    Met   Glu   Ser   Ser   Leu   Gly   Gly   Val   Leu
                                     1                        5

CTG   ATT   TTG   TGG   CTT   CAA   GTG   GAC   TGG   GTG   AAG   AGC   CAA   AAG   ATA   GAA   142
Leu   Ile   Leu   Trp   Leu   Gln   Val   Asp   Trp   Val   Lys   Ser   Gln   Lys   Ile   Glu
10                            15                      20                            25

CAG   AAT   TCC   GAG   GCC   CTG   AAC   ATT   CAG   GAG   GGT   AAA   ACG   GCC   ACC   CTG   190
Gln   Asn   Ser   Glu   Ala   Leu   Asn   Ile   Gln   Glu   Gly   Lys   Thr   Ala   Thr   Leu
                        30                            35                            40

ACC   TGC   AAC   TAT   ACA   AAC   TAT   TCT   CCA   GCA   TAC   TTA   CAG   TGG   TAC   CGA   238
Thr   Cys   Asn   Tyr   Thr   Asn   Tyr   Ser   Pro   Ala   Tyr   Leu   Gln   Trp   Tyr   Arg
                        45                            50                            55

CAA   GAT   CCA   GGA   AGA   GGC   CCT   GTT   TTC   TTG   CTA   CTC   ATA   CGT   GAA   AAT   286
Gln   Asp   Pro   Gly   Arg   Gly   Pro   Val   Phe   Leu   Leu   Leu   Ile   Arg   Glu   Asn
                  60                            65                      70

GAG   AAA   GAA   AAA   AGG   AAA   GAA   AGA   CTG   AAG   GTC   ACC   TTT   GAT   ACC   ACC   334
Glu   Lys   Glu   Lys   Arg   Lys   Glu   Arg   Leu   Lys   Val   Thr   Phe   Asp   Thr   Thr
      75                            80                            85

CTT   AAA   CAG   AGT   TTG   TTT   CAT   ATC   ACA   GCC   TCC   CAG   CCT   GCA   GAC   TCA   382
Leu   Lys   Gln   Ser   Leu   Phe   His   Ile   Thr   Ala   Ser   Gln   Pro   Ala   Asp   Ser
90                            95                      100                           105

GCT   ACC   TAC   CTC   TGT   GCT                                                             400
Ala   Thr   Tyr   Leu   Cys   Ala
                        110
```

( 2 ) INFORMATION FOR SEQ ID NO: 9:

( i ) SEQUENCE CHARACTERISTICS:
    ( A ) LENGTH: 386
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: IGR a 11
    ( B ) LOCATION:
    ( C ) IDENTIFICATION METHOD:
    ( D ) OTHER INFORMATION: SEQUENCE V Alpha 7

( x i ) SEQUENCE DESCRIPTION: SEQ ID NO:9:

```
              GCCTTCTGCA   GACTCCAATG   GCTCAGGAAC   TGGGAATGCA   GTGCCAGGCT              50

CGTGGTATCC   TGCAGCAG  ATG   TGG   GGA   GTT   TTC   CTT   CTT   TAT   GTT   95
                                     Met   Trp   Gly   Val   Phe   Leu   Leu   Tyr   Val
                                      1                       5

TCC   ATG   AAG   ATG   GGA   GGC   ACT   ACA   GGA   CAA   AAC   ATT   GAC   CAG   CCC   ACT   143
```

| | | | | | | | | | | | | | | | |
|---|---|---|---|---|---|---|---|---|---|---|---|---|---|---|---|
|Ser|Met|Lys|Met|Gly|Gly|Thr|Thr|Gly|Gln|Asn|Ile|Asp|Gln|Pro|Thr|
|10| | | |15| | | |20| | | | | |25| |

```
GAG  ATG  ACA  GCT  ACG  GAA  GGT  GCC  ATT  GTC  CAG  ATC  AAC  TGC  ACG  TAC    191
Glu  Met  Thr  Ala  Thr  Glu  Gly  Ala  Ile  Val  Gln  Ile  Asn  Cys  Thr  Tyr
               30                        35                        40

CAG  ACA  TCT  GGG  TTC  AAC  GGG  CTG  TTC  TGG  TAC  CAG  CAA  CAT  GCT  GGC    239
Gln  Thr  Ser  Gly  Phe  Asn  Gly  Leu  Phe  Trp  Tyr  Gln  Gln  His  Ala  Gly
               45                        50                        55

GAA  GCA  CCC  ACA  TTT  CTG  TCT  TAC  AAT  GTT  CTG  GAT  GGT  TTG  GAG  GAG    287
Glu  Ala  Pro  Thr  Phe  Leu  Ser  Tyr  Asn  Val  Leu  Asp  Gly  Leu  Glu  Glu
          60                       65                        70

AAA  GGT  CGT  TTT  TCT  TCA  TTC  CTT  AGT  CGG  TCT  AAA  GGG  TAC  AGT  TAC    335
Lys  Gly  Arg  Phe  Ser  Ser  Phe  Leu  Ser  Arg  Ser  Lys  Gly  Tyr  Ser  Tyr
     75                            80                        85

CTC  CTT  TTG  AAG  GAG  CTC  CAG  ATG  AAA  GAC  TCT  GCC  TCT  TAC  CTC  TGT    383
Leu  Leu  Leu  Lys  Glu  Leu  Gln  Met  Lys  Asp  Ser  Ala  Ser  Tyr  Leu  Cys
90                       95                       100                      105

GCT                                                                                386
Ala
```

( 2 ) INFORMATION FOR SEQ ID NO: 10:

( i ) SEQUENCE CHARACTERISTICS:
        ( A ) LENGTH: 383
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 12
        ( B ) LOCATION:
        ( C ) IDENTIFICATION METHOD:
        ( D ) OTHER INFORMATION: SEQUENCE V Alpha 22

( x i ) SEQUENCE DESCRIPTION: SEQ ID NO:10:

```
          TGTGACTTCT  TCATGTTAAG  GATCAAGACC  ATTATTGGG  TAACACACTA              50

AAG  ATG  AAC  TAT  TCT  CCA  GGC  TTA  GTA  TCT  CTG  ATA  CTC  TTA  CTG     95
          Met  Asn  Tyr  Ser  Pro  Gly  Leu  Val  Ser  Leu  Ile  Leu  Leu  Leu
          1                   5                        10

CTT  GGA  AGA  ACC  CGT  GGA  GAT  TCA  GTG  ACC  CAG  ATG  GAA  GGG  CCA  GTG    143
Leu  Gly  Arg  Thr  Arg  Gly  Asp  Ser  Val  Thr  Gln  Met  Glu  Gly  Pro  Val
15                       20                        25                       30

ACT  CTC  TCA  GAA  GAG  GCC  TTC  CTG  ACT  ATA  AAC  TGC  ACG  TAC  ACA  GCC    191
Thr  Leu  Ser  Glu  Glu  Ala  Phe  Leu  Thr  Ile  Asn  Cys  Thr  Tyr  Thr  Ala
                    35                        40                       45

ACA  GGA  TAC  CCT  TCC  CTT  TTC  TGG  TAT  GTC  CAA  TAT  CCT  GGA  GAA  GGT    239
Thr  Gly  Tyr  Pro  Ser  Leu  Phe  Trp  Tyr  Val  Gln  Tyr  Pro  Gly  Glu  Gly
               50                       55                       60

CTA  CAG  CTC  CTC  CTG  AAA  GCC  ACG  AAG  GCT  GAT  GAC  AAG  GGA  AGC  AAC    287
Leu  Gln  Leu  Leu  Leu  Lys  Ala  Thr  Lys  Ala  Asp  Asp  Lys  Gly  Ser  Asn
          65                       70                       75

AAA  GGT  TTT  GAA  GCC  ACA  TAC  CGT  AAA  GAA  ACC  ACT  TCT  TTC  CAC  TTG    335
Lys  Gly  Phe  Glu  Ala  Thr  Tyr  Arg  Lys  Glu  Thr  Thr  Ser  Phe  His  Leu
```

```
                       80                            85                            90
GAG  AAA  GGC  TCA  GTT  CAA  GTG  TCA  GAC  TCA  GCG  GTG  TAC  TTC  TGT  GCT              383
Glu  Lys  Gly  Ser  Val  Gln  Val  Ser  Asp  Ser  Ala  Val  Tyr  Phe  Cys  Ala
95                       100                           105                      110
```

( 2 ) INFORMATION FOR SEQ ID NO: 11:

( i ) SEQUENCE CHARACTERISTICS:
        ( A ) LENGTH: 364
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 13
        ( B ) LOCATION:
        ( C ) IDENTIFICATION METHOD:
        ( D ) OTHER INFORMATION: SEQUENCE V Alpha 16

( x i ) SEQUENCE DESCRIPTION: SEQ ID NO:11:

```
                    AATCCCGCCC   GCCGTGAGCT   TAGCTGGAGC  C  ATG  GCC  TCT  GCA  CCC              46
                                                             Met  Ala  Ser  Ala  Pro
                                                             1                    5

ATC  TCG  ATG  CTT  GCG  ATG  CTC  TTC  ACA  TTG  AGT  GGG  CTG  AGA  GCT  CAG              94
Ile  Ser  Met  Leu  Ala  Met  Leu  Phe  Thr  Leu  Ser  Gly  Leu  Arg  Ala  Gln
               10                      15                           20

TCA  GTG  GCT  CAG  CCG  GAA  GAT  CAG  GTC  AAC  GTT  GCT  GAA  GGG  AAT  CCT              142
Ser  Val  Ala  Gln  Pro  Glu  Asp  Gln  Val  Asn  Val  Ala  Glu  Gly  Asn  Pro
                    25                      30                      35

CTG  ACT  GTG  AAA  TGC  ACC  TAT  TCA  GTC  TCT  GGA  AAC  CCT  TAT  CTT  TTT              190
Leu  Thr  Val  Lys  Cys  Thr  Tyr  Ser  Val  Ser  Gly  Asn  Pro  Tyr  Leu  Phe
          40                      45                           50

TGG  TAT  GTT  CAA  TAC  CCC  AAC  CGA  GGC  CTC  CAG  TTC  CTT  CTG  AAA  TAC              238
Trp  Tyr  Val  Gln  Tyr  Pro  Asn  Arg  Gly  Leu  Gln  Phe  Leu  Leu  Lys  Tyr
     55                      60                      65

ATC  ACA  GGG  GAT  AAC  CTG  GTT  AAA  GGC  AGC  TAT  GGC  TTT  GAA  GCT  GAA              286
Ile  Thr  Gly  Asp  Asn  Leu  Val  Lys  Gly  Ser  Tyr  Gly  Phe  Glu  Ala  Glu
70                       75                      80                           85

TTT  AAC  AAG  AGC  CAA  ACC  TCC  TTC  CAC  CTG  AAG  AAA  CCA  TCT  GCC  CTT              334
Phe  Asn  Lys  Ser  Gln  Thr  Ser  Phe  His  Leu  Lys  Lys  Pro  Ser  Ala  Leu
                    90                      95                      100

GTG  AGC  GAC  TCC  GCT  TTG  TAC  TTC  TGT  GCT                                             364
Val  Ser  Asp  Ser  Ala  Leu  Tyr  Phe  Cys  Ala
               105                      110
```

( 2 ) INFORMATION FOR SEQ ID NO: 12:

( i ) SEQUENCE CHARACTERISTICS:
        ( A ) LENGTH: 263
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:

(A) ORGANISM: HUMAN
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE: HUMAN T LYMPHOCYTE
            (I) ORGANELLE:

(ix) FEATURE:
            (A) NAME/KEY: Ja 01
            (B) LOCATION:
            (C) IDENTIFICATION METHOD:
            (D) OTHER INFORMATION: SEQUENCE J Alpha (xi) SEQUENCE DESCRIPTION: SEQ ID NO:12:

```
CCTTCAAGGA  AAATTAAGGC  AAATAGAATT  GGGCTGGGGA  GTTGCTACTT  ATTAGTATTC        60

CTCCCACGTT  CTAACCTAAT  TATAAGGAGG  TTGTTTTGGC  CATGGGCAGT  CATCTCAGGT       120

TTTGTTTTCC  TGCTTTCCTC  CCTAACCTCC  ACCTGTCTTC  CTAGAGGCCT  GAGTCAAGGT       180

TATTGCAATA  GCACTAAAGA  CTGTGT  AAC ACC AAT GCA GGC AAA TCA ACC TTT          233
                                Asn Thr Asn Ala Gly Lys Ser Thr Phe
                                 1                5

GGG GAT GGG ACT ACG CTC ACT GTG AAG CCA                                      263
Gly Asp Gly Thr Thr Leu Thr Val Lys Pro
10                  15
```

(2) INFORMATION FOR SEQ ID NO: 13:

(i) SEQUENCE CHARACTERISTICS:
            (A) LENGTH: 277
            (B) TYPE: NUCLEOTIDE
            (C) STRANDEDNESS: DOUBLE
            (D) TOPOLOGY: LINEAR (ii) MOLECULE TYPE: cDNA to mRNA (vi) ORIGINAL SOURCE:
            (A) ORGANISM: HUMAN
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE: HUMAN T LYMPHOCYTE
            (I) ORGANELLE:

(ix) FEATURE:
            (A) NAME/KEY: Ja 02
            (B) LOCATION:
            (C) IDENTIFICATION METHOD:
            (D) OTHER INFORMATION: SEQUENCE J Alpha (xi) SEQUENCE DESCRIPTION: SEQ ID NO:13:

```
AAGGACACAG  ACTGCCTGCA  TGAAGGCTGG  AGCTGGGCCC  AGGATGAGGA  AAGGCCTCAG        60

GAAGGAAGGG  CTGACACGAA  ATAAGGAATA  CCATGGCATT  CATGAGATGT  GCGTCTGAAT       120

CCTCTCTCTT  GCCTGAGAAG  CTTTAGCTTC  CACCTTGAGA  CACAAAACAT  GTGGTTATGA       180

AGAGATGACA  AGGTTTTTGT  AAAAGAATGA  GCCATTGTGG  ATA GGC TTT GGG AAT          235
                                                Ile Gly Phe Gly Asn
                                                 1                5

GTG CTG CAT TGC GGG TCC GGC ACT CAA GTG ATT GTT TTA CCA                      277
Val Leu His Cys Gly Ser Gly Thr Gln Val Ile Val Leu Pro
10                  15
```

(2) INFORMATION FOR SEQ ID NO: 15:

(i) SEQUENCE CHARACTERISTICS:

(A) LENGTH: 60
(B) TYPE: NUCLEOTIDE
(C) STRANDEDNESS: DOUBLE
(D) TOPOLOGY: LINEAR (ii) MOLECULE TYPE: cDNA to mRNA (vi) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE: HUMAN T LYMPHOCYTE
(I) ORGANELLE:

(ix) FEATURE:
(A) NAME/KEY: Ja 04
(B) LOCATION:
(C) IDENTIFICATION METHOD:
(D) OTHER INFORMATION: SEQUENCE J Alpha (xi) SEQUENCE DESCRIPTION: SEQ ID NO:15:

```
TA  GAT ACT GGA GGC TTC AAA ACT ATC TTT GGA GCA GGA ACA AGA CTA     47
    Asp Thr Gly Gly Phe Lys Thr Ile Phe Gly Ala Gly Thr Arg Leu
    1               5                   10                  15

TTT GTT AAA GCA A                                                   60
Phe Val Lys Ala
```

(2) INFORMATION FOR SEQ ID NO: 16:

(i) SEQUENCE CHARACTERISTICS:
(A) LENGTH: 59
(B) TYPE: NUCLEOTIDE
(C) STRANDEDNESS: DOUBLE
(D) TOPOLOGY: LINEAR (ii) MOLECULE TYPE: cDNA to mRNA (vi) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE: HUMAN T LYMPHOCYTE
(I) ORGANELLE:

(ix) FEATURE:
(A) NAME/KEY: Ja 05
(B) LOCATION:
(C) IDENTIFICATION METHOD:
(D) OTHER INFORMATION: SEQUENCE J Alpha (xi) SEQUENCE DESCRIPTION: SEQ ID NO:16:

```
C   CTA ACT GGG GCA AAC AAC GTC TTC TTT GGG ACT GGA ACG AGA CTC     46
    Leu Thr Gly Ala Asn Asn Val Phe Phe Gly Thr Gly Thr Arg Leu
    1               5                   10                  15

ACC GTT CTT CCC T                                                   59
Thr Val Leu Pro
```

(2) INFORMATION FOR SEQ ID NO: 17:

(i) SEQUENCE CHARACTERISTICS:
(A) LENGTH: 60
(B) TYPE: NUCLEOTIDE
(C) STRANDEDNESS: DOUBLE
(D) TOPOLOGY: LINEAR (ii) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: Ja 06
    ( B ) LOCATION:
    ( C ) IDENTIFICATION METHOD:
    ( D ) OTHER INFORMATION: SEQUENCE J Alpha ( x i ) SEQUENCE DESCRIPTION: SEQ ID NO:17:

```
AT  GGA  GGA  AGC  CAA  GGA  AAT  CTC  ATC  TTT  GGA  AAA  GGC  ACT  AAA  CTC         47
    Gly  Gly  Ser  Gln  Gly  Asn  Leu  Ile  Phe  Gly  Lys  Gly  Thr  Lys  Leu
    1              5                        10                        15

TCT  GTT  AAA  CCA  A                                                                  60
Ser  Val  Lys  Pro
```

( 2 ) INFORMATION FOR SEQ ID NO: 18:

( i ) SEQUENCE CHARACTERISTICS:
    ( A ) LENGTH: 56
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: Ja 07
    ( B ) LOCATION:
    ( C ) IDENTIFICATION METHOD:
    ( D ) OTHER INFORMATION: SEQUENCE J Alpha ( x i ) SEQUENCE DESCRIPTION: SEQ ID NO:18:

```
GGA  GCC  AAT  AGT  AAG  CTG  ACA  TTT  GGA  AAA  GGA  ATA  ACT  CTG  AGT  GTT        48
Gly  Ala  Asn  Ser  Lys  Leu  Thr  Phe  Gly  Lys  Gly  Ile  Thr  Leu  Ser  Val
1              5                        10                        15

AGA  CCA  GA                                                                           56
Arg  Pro
```

( 2 ) INFORMATION FOR SEQ ID NO: 19:

( i ) SEQUENCE CHARACTERISTICS:
    ( A ) LENGTH: 57
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:

```
            ( E ) HAPLOTYPE:
            ( F ) TISSUE TYPE:
            ( G ) CELL TYPE:
            ( H ) CELL LINE: HUMAN T LYMPHOCYTE
            ( I ) ORGANELLE:

( i x ) FEATURE:
            ( A ) NAME/KEY: Ja 08
            ( B ) LOCATION:
            ( C ) IDENTIFICATION METHOD:
            ( D ) OTHER INFORMATION: SEQUENCE J Alpha ( x i ) SEQUENCE DESCRIPTION: SEQ ID NO:19:
```

```
CT  GGT  GGC  TAC  AAT  AAG  CTG  ATT  TTT  GGA  GCA  GGG  ACC  AGG  CTG  GCT         47
    Gly  Gly  Tyr  Asn  Lys  Leu  Ile  Phe  Gly  Ala  Gly  Thr  Arg  Leu  Ala
    1              5                       10                      15

GTA  CAC  CCA  T                                                                       57
Val  His  Pro
```

( 2 ) INFORMATION FOR SEQ ID NO: 20:

```
        ( i ) SEQUENCE CHARACTERISTICS:
                ( A ) LENGTH: 50
                ( B ) TYPE: NUCLEOTIDE
                ( C ) STRANDEDNESS: DOUBLE
                ( D ) TOPOLOGY: LINEAR ( i i ) MOLECULE TYPE: cDNA to mRNA ( v i ) ORIGINAL SOURCE:
                ( A ) ORGANISM: HUMAN
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE: HUMAN T LYMPHOCYTE
                ( I ) ORGANELLE:

( i x ) FEATURE:
                ( A ) NAME/KEY: Ja 09
                ( B ) LOCATION:
                ( C ) IDENTIFICATION METHOD:
                ( D ) OTHER INFORMATION: SEQUENCE J Alpha ( x i ) SEQUENCE DESCRIPTION: SEQ ID NO:20:
```

```
T  GGA  AAC  AAG  CTG  GTC  TTT  GGC  GCA  GGA  ACC  ATT  CTG  AGA  GTC  AAG           46
   Gly  Asn  Lys  Leu  Val  Phe  Gly  Ala  Gly  Thr  Ile  Leu  Arg  Val  Lys
   1              5                       10                      15

TCC  T                                                                                  50
Ser
```

( 2 ) INFORMATION FOR SEQ ID NO: 21:

```
        ( i ) SEQUENCE CHARACTERISTICS:
                ( A ) LENGTH: 22
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( B ) LOCATION:
                ( C ) IDENTIFICATION METHOD:
                ( D ) OTHER INFORMATION: A ( x i ) SEQUENCE DESCRIPTION: SEQ ID NO:21:
```

```
GTTGCTCCAG  GCCACAGCAC  TG                                                              22
```

( 2 ) INFORMATION FOR SEQ ID NO: 22:

( i ) SEQUENCE CHARACTERISTICS:
        ( A ) LENGTH: 35
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: POLY C ( x i ) SEQUENCE DESCRIPTION: SEQ ID NO:22:

GCATGCGCGC GGCCGCGGAG GCCCCCCCCC CCCCC       35

( 2 ) INFORMATION FOR SEQ ID NO: 23:

( i ) SEQUENCE CHARACTERISTICS:
        ( A ) LENGTH: 26
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: B ( x i ) SEQUENCE DESCRIPTION: SEQ ID NO:23:

GTCCATAGAC CTCATGTCCA GCACAG       26

( 2 ) INFORMATION FOR SEQ ID NO: 24:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: C ( x i ) SEQUENCE DESCRIPTION: SEQ ID NO:24:

ATACACATCA GAATTCTTAC TTTG       24

( 2 ) INFORMATION FOR SEQ ID NO: 25:

( i ) SEQUENCE CHARACTERISTICS:
        ( A ) LENGTH: 19
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: D ( x i ) SEQUENCE DESCRIPTION: SEQ ID NO:25:

GTCACTGGAT TTAGAGTCT  19

(2) INFORMATION FOR SEQ ID NO: 26:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 1, CLONE AB22, POSITION
            235, THE 6TH AND 23RD NUCLEOTIDES CORRESPOND
            TO MISMATCHES INTRODUCED RELATIVE TO THE NATURAL
            SEQUENCE ( x i ) SEQUENCE DESCRIPTION: SEQ ID NO:26:

GGCATTAACG GTTTTGAGGC TGGA  24

(2) INFORMATION FOR SEQ ID NO: 27:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 2, CLONE IGRa09,
            POSITION 93*, THE 24TH NUCLEOTIDE CORRESPONDS TO
            A MISMATCH INTRODUCED RELATIVE TO THE
            NATURAL SEQUENCE ( x i ) SEQUENCE DESCRIPTION: SEQ ID NO:27:

CAGTGTTCCA GAGGGAGCCA TTGC  24

(2) INFORMATION FOR SEQ ID NO: 28:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 3, CLONE HAP05, POSITION
            297

( x i ) SEQUENCE DESCRIPTION: SEQ ID NO:28:

CCGGGCAGCA GACACTGCTT CTTA  24

(2) INFORMATION FOR SEQ ID NO: 29:

( i ) SEQUENCE CHARACTERISTICS:
        ( A ) LENGTH: 24
        ( B ) TYPE: NUCLEOTIDE
        ( C ) STRANDEDNESS: SINGLE (D) TOPOLOGY: LINEAR (i i) MOLECULE TYPE: OLIGONUCLEOTIDE (i x) FEATURE:
    (A) NAME/KEY:
    (B) LOCATION:
    (C) IDENTIFICATION METHOD:
    (D) OTHER INFORMATION: TYPE V Alpha 4, CLONE HAP08, POSITION 153

(x i) SEQUENCE DESCRIPTION: SEQ ID NO:29:

TTGGTATCGA CAGCTTCCCT CCCA      24

(2) INFORMATION FOR SEQ ID NO: 30:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (i i) MOLECULE TYPE: OLIGONUCLEOTIDE (i x) FEATURE:
    (A) NAME/KEY:
    (B) LOCATION:
    (C) IDENTIFICATION METHOD:
    (D) OTHER INFORMATION: TYPE V Alpha 5, CLONE IGRa10, POSITION 113

(x i) SEQUENCE DESCRIPTION: SEQ ID NO:30:

CGGCCACCCT GACCTGCAAC TATA      24

(2) INFORMATION FOR SEQ ID NO: 31:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (i i) MOLECULE TYPE: OLIGONUCLEOTIDE (i x) FEATURE:
    (A) NAME/KEY:
    (B) LOCATION:
    (C) IDENTIFICATION METHOD:
    (D) OTHER INFORMATION: TYPE V Alpha 6, CLONE HAP01, POSITION 287

(x i) SEQUENCE DESCRIPTION: SEQ ID NO:31:

TCCGCCAACC TTGTCATCTC CGCT      24

(2) INFORMATION FOR SEQ ID NO: 32:

(i) SEQUENCE CHARACTERISTICS:
    (A) LENGTH: 24
    (B) TYPE: NUCLEOTIDE
    (C) STRANDEDNESS: SINGLE
    (D) TOPOLOGY: LINEAR (i i) MOLECULE TYPE: OLIGONUCLEOTIDE (i x) FEATURE:
    (A) NAME/KEY:
    (B) LOCATION:
    (C) IDENTIFICATION METHOD:
    (D) OTHER INFORMATION: TYPE V Alpha 7, CLONE IGRa11, POSITION 159, THE 9TH AND 15TH NUCLEOTIDES CORRESPOND TO MISMATCHES INTRODUCED RELATIVE TO THE NATURAL SEQUENCE (x i) SEQUENCE DESCRIPTION: SEQ ID NO:32:

GCAACATGCT GGCGGAGCAC CCAC 24

( 2 ) INFORMATION FOR SEQ ID NO: 33:

( i ) SEQUENCE CHARACTERISTICS:
　　　　　　　　( A ) LENGTH: 24
　　　　　　　　( B ) TYPE: NUCLEOTIDE
　　　　　　　　( C ) STRANDEDNESS: SINGLE
　　　　　　　　( D ) TOPOLOGY: LINEAR ( i i ) MOLECULE TYPE: OLIGONUCLEOTIDE ( i x ) FEATURE:
　　　　　　　　( A ) NAME/KEY:
　　　　　　　　( B ) LOCATION:
　　　　　　　　( C ) IDENTIFICATION METHOD:
　　　　　　　　( D ) OTHER INFORMATION: TYPE V Alpha 8, CLONE HAP41, POSITION
　　　　　　　　　　　204

( x i ) SEQUENCE DESCRIPTION: SEQ ID NO:33:

CATTCGTTCA AATGTGGGCA AAAG 24

( 2 ) INFORMATION FOR SEQ ID NO: 34:

( i ) SEQUENCE CHARACTERISTICS:
　　　　　　　　( A ) LENGTH: 24
　　　　　　　　( B ) TYPE: NUCLEOTIDE
　　　　　　　　( C ) STRANDEDNESS: SINGLE
　　　　　　　　( D ) TOPOLOGY: LINEAR ( i i ) MOLECULE TYPE: OLIGONUCLEOTIDE ( i x ) FEATURE:
　　　　　　　　( A ) NAME/KEY:
　　　　　　　　( B ) LOCATION:
　　　　　　　　( C ) IDENTIFICATION METHOD:
　　　　　　　　( D ) OTHER INFORMATION: TYPE V Alpha 9, CLONE HAVP36,
　　　　　　　　　　　POSITION 168, THE 22ND NUCLEOTIDE CORRESPONDS TO A
　　　　　　　　　　　MISMATCH INTRODUCED RELATIVE TO THE NATURAL SEQUENCE ( x i ) SEQUENCE DESCRIPTION: SEQ ID NO:34:

CCAGTACTCC AGACAACGCC TGCA 24

( 2 ) INFORMATION FOR SEQ ID NO: 35:

( i ) SEQUENCE CHARACTERISTICS:
　　　　　　　　( A ) LENGTH: 24
　　　　　　　　( B ) TYPE: NUCLEOTIDE
　　　　　　　　( C ) STRANDEDNESS: SINGLE
　　　　　　　　( D ) TOPOLOGY: LINEAR ( i i ) MOLECULE TYPE: OLIGONUCLEOTIDE ( i x ) FEATURE:
　　　　　　　　( A ) NAME/KEY:
　　　　　　　　( B ) LOCATION:
　　　　　　　　( C ) IDENTIFICATION METHOD:
　　　　　　　　( D ) OTHER INFORMATION: TYPE V Alpha 10, CLONE HAP58,
　　　　　　　　　　　POSITION 282

( x i ) SEQUENCE DESCRIPTION: SEQ ID NO:35:

CACTGCGGCC CAGCCTGGTG ATAC 24

( 2 ) INFORMATION FOR SEQ ID NO: 36:

( i ) SEQUENCE CHARACTERISTICS:
　　　　　　　　( A ) LENGTH: 24
　　　　　　　　( B ) TYPE: NUCLEOTIDE
　　　　　　　　( C ) STRANDEDNESS: SINGLE
　　　　　　　　( D ) TOPOLOGY: LINEAR ( i i ) MOLECULE TYPE: OLIGONUCLEOTIDE ( i x ) FEATURE:
    ( A ) NAME/KEY:
    ( B ) LOCATION:
    ( C ) IDENTIFICATION METHOD:
    ( D ) OTHER INFORMATION: TYPE V Alpha 11, CLONE AB19, POSITION 254*

( x i ) SEQUENCE DESCRIPTION: SEQ ID NO:36:

CGCTGCTCAT CCTCCAGGTG CGGG 24

( 2 ) INFORMATION FOR SEQ ID NO: 37:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 12, CLONE V12MA483, POSITION 213

( x i ) SEQUENCE DESCRIPTION: SEQ ID NO:37:

TCGTCGGAAC TCTTTTGATG AGCA 24

( 2 ) INFORMATION FOR SEQ ID NO: 38:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 13, CLONE HAVT15, POSITION 152*

( x i ) SEQUENCE DESCRIPTION: SEQ ID NO:38:

TTCATCAAAA CCCTTGGGGA CAGC 24

( 2 ) INFORMATION FOR SEQ ID NO: 39:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V Alpha 14, CLONE HAVT20, POSITION 181

( x i ) SEQUENCE DESCRIPTION: SEQ ID NO:39:

CCCAGCAGGC AGATGATTCT CGTT 24

( 2 ) INFORMATION FOR SEQ ID NO: 40:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( B ) LOCATION:
    ( C ) IDENTIFICATION METHOD:
    ( D ) OTHER INFORMATION: TYPE V Alpha 15, CLONE HAVT31,
        POSITION 278, THE 12TH NUCLEOTIDE CORRESPONDS TO A
        MISMATCH INTRODUCED RELATIVE TO THE NATURAL SEQUENCE ( x i ) SEQUENCE DESCRIPTION: SEQ ID NO:40:

TTGCAGACAC CGAGACTGGG GACT    24

( 2 ) INFORMATION FOR SEQ ID NO: 41:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( B ) LOCATION:
    ( C ) IDENTIFICATION METHOD:
    ( D ) OTHER INFORMATION: TYPE V Alpha 16, CLONE IGRa13,
        POSITION 89

( x i ) SEQUENCE DESCRIPTION: SEQ ID NO:41:

TCAACGTTGC TGAAGGGAAT CCTC    24

( 2 ) INFORMATION FOR SEQ ID NO: 42:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( B ) LOCATION:
    ( C ) IDENTIFICATION METHOD:
    ( D ) OTHER INFORMATION: TYPE V Alpha 17, CLONE AB11,
        POSITION 204, THE 12TH NUCLEOTIDE CORRESPONDS TO
        A MISMATCH INTRODUCED RELATIVE TO THE NATURAL SEQUENCE ( x i ) SEQUENCE DESCRIPTION: SEQ ID NO:42:

TGGGAAAGGC CGTGCATTAT TGAT    24

( 2 ) INFORMATION FOR SEQ ID NO: 43:

( i ) SEQUENCE CHARACTERISTICS:
    ( A ) LENGTH: 24
    ( B ) TYPE: NUCLEOTIDE
    ( C ) STRANDEDNESS: SINGLE
    ( D ) TOPOLOGY: LINEAR ( i i ) MOLECULE TYPE: OLIGONUCLEOTIDE ( i x ) FEATURE:
    ( A ) NAME/KEY:
    ( B ) LOCATION:

(C) IDENTIFICATION METHOD:
(D) OTHER INFORMATION: TYPE V Alpha 18, CLONE AB21, POSITION
114

(xi) SEQUENCE DESCRIPTION: SEQ ID NO:43:

CAGCACCAAT TTCACCTGCA GCTT                                                      24

(2) INFORMATION FOR SEQ ID NO: 44:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 19, CLONE AC24, POSITION
            162

(xi) SEQUENCE DESCRIPTION: SEQ ID NO:44:

ACACTGGCTG CAACAGCATC CAGG                                                      24

(2) INFORMATION FOR SEQ ID NO: 45:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 20, CLONE AE212,
            POSITION 232

(xi) SEQUENCE DESCRIPTION: SEQ ID NO:45:

TCCCTGTTTA TCCCTGCCGA CAGA                                                      24

(2) INFORMATION FOR SEQ ID NO: 46:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE V Alpha 21, CLONE AF211,
            POSITION 92

(xi) SEQUENCE DESCRIPTION: SEQ ID NO:46:

AGCAAAATTC ACCATCCCTG AGCG                                                      24

(2) INFORMATION FOR SEQ ID NO: 47:

(i) SEQUENCE CHARACTERISTICS:
        (A) LENGTH: 24
        (B) TYPE: NUCLEOTIDE (C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE V Alpha 22, CLONE IGRa12, POSITION 197

(xi) SEQUENCE DESCRIPTION: SEQ ID NO:47:

CCTGAAAGCC ACGAAGGCTG ATGA  24

(2) INFORMATION FOR SEQ ID NO: 48:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE V Alpha w23, CLONE IGRa01, POSITION 246

(xi) SEQUENCE DESCRIPTION: SEQ ID NO:48:

TGCCTCGCTG GATAAATCAT CAGG  24

(2) INFORMATION FOR SEQ ID NO: 49:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE V Alpha w24, CLONE IGRa02, POSITION 259, THE 21ST NUCLEOTIDE CORRESPONDS TO A MISMATCH INTRODUCED RELATIVE TO THE NATURAL SEQUENCE (xi) SEQUENCE DESCRIPTION: SEQ ID NO:49:

CTGGATGCAG ACACAAAGCA GAGC  24

(2) INFORMATION FOR SEQ ID NO: 50:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE V Alpha w25, CLONE IGRA03, POSITION 148, THE 7TH AND 17TH NUCLEOTIDES CORRESPOND TO MISMATCHES INTRODUCED RELATIVE TO THE NATURAL SEQUENCE (x i) SEQUENCE DESCRIPTION:SEQ ID NO:50:

TGGCTACGGT ACAAGCCGGA CCCT 24

(2) INFORMATION FOR SEQ ID NO: 51:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE V Alpha w26, CLONE IGRa04,
            POSITION 299, THE 4TH AND 20TH NUCLEOTIDES
            CORRESPOND TO MISMATCHES INTRODUCED RELATIVE TO THE
            NATURAL SEQUENCE (x i) SEQUENCE DESCRIPTION: SEQ ID NO:51:

AGCGCAGCCA TGCAGGCATG TACC 24

(2) INFORMATION FOR SEQ ID NO: 52:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE V Alpha w27, CLONE IGRa05,
            POSITION 268*

(x i) SEQUENCE DESCRIPTION: SEQ ID NO:52:

AAGCCCGTCT CAGCACCCTC CACA 24

(2) INFORMATION FOR SEQ ID NO: 53:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE V Alpha w28, CLONE IGRa06,
            POSITION 95, THE 8TH AND 15TH NUCLEOTIDES
            CORRESPOND TO MISMATCHES INTRODUCED RELATIVE TO THE
            NATURAL SEQUENCE (x i) SEQUENCE DESCRIPTION: SEQ ID NO:53:

TGGTTGTGCA CGAGCGAGAC ACTG 24

(2) INFORMATION FOR SEQ ID NO: 54:

(i) SEQUENCE CHARACTERISTICS:
        (A) LENGTH: 24

(B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE V Alpha w29, CLONE IGRa07,
            POSITION 210

(x i) SEQUENCE DESCRIPTION: SEQ ID NO:54:

GAAGGGTGGA GAACAGATGC GTCG 24

(2) INFORMATION FOR SEQ ID NO: 55:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE C Alpha A, POSITION 129

(x i) SEQUENCE DESCRIPTION: SEQ ID NO:55:

ATACACATCA GAATTCTTAC TTTG 24

(2) INFORMATION FOR SEQ ID NO: 56:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE C Alpha B, POSITION 201

(x i) SEQUENCE DESCRIPTION: SEQ ID NO:56:

GTTGCTCCAG GCCGCGGCAC TGTT 24

(2) INFORMATION FOR SEQ ID NO: 57:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (i i) MOLECULE TYPE: OLIGONUCLEOTIDE (i x) FEATURE:
        (A) NAME/KEY:
        (B) LOCATION:
        (C) IDENTIFICATION METHOD:
        (D) OTHER INFORMATION: TYPE C Alpha C, POSITION 57

(x i) SEQUENCE DESCRIPTION: SEQ ID NO:57:

GTCACTGGAT TTAGAGTCT 19

( 2 ) INFORMATION FOR SEQ ID NO: 58:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Act 1, CLONE Beta-actin,
            POSITION 1161

( x i ) SEQUENCE DESCRIPTION: SEQ ID NO:58:

ATTTGCGGTG GACGATGGAG GGGC　　　　　　　　　　　　　　　　　　　　　　　24

( 2 ) INFORMATION FOR SEQ ID NO: 59:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Act 2, CLONE Beta-ACTIN,
            POSITION 261

( x i ) SEQUENCE DESCRIPTION: SEQ ID NO:59:

GGCATCGTCA CCAACTGGGA CGAC　　　　　　　　　　　　　　　　　　　　　　　24

( 2 ) INFORMATION FOR SEQ ID NO: 60:

( i ) SEQUENCE CHARACTERISTICS:
        ( A ) LENGTH: 19
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Act 3, CLONE Beta-ACTIN,
            POSITION 642

( x i ) SEQUENCE DESCRIPTION: SEQ ID NO:60:

ACCACCACGG CGGAGCGGG　　　　　　　　　　　　　　　　　　　　　　　　　19

( 2 ) INFORMATION FOR SEQ ID NO: 61:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:

-continued (C) IDENTIFICATION METHOD:
(D) OTHER INFORMATION: TYPE C Beta F, POSITION 135

(x i) SEQUENCE DESCRIPTION: SEQ ID NO:61:

CGGGCTGCTC CTTGAGGGGC TGCG                                                     24

(2) INFORMATION FOR SEQ ID NO: 62:

(i) SEQUENCE CHARACTERISTICS:
(A) LENGTH: 19
(B) TYPE: NUCLEOTIDE
(C) STRANDEDNESS: SINGLE
(D) TOPOLOGY: LINEAR (i i) MOLECULE TYPE: OLIGONUCLEOTIDE (i x) FEATURE:
(A) NAME/KEY:
(B) LOCATION:
(C) IDENTIFICATION METHOD:
(D) OTHER INFORMATION: TYPE C Beta K, POSITION 20

(x i) SEQUENCE DESCRIPTION: SEQ ID NO:62:

CCCACCCGAG GTCGCTGTG                                                           19

(2) INFORMATION FOR SEQ ID NO: 63:

(i) SEQUENCE CHARACTERISTICS:
(A) LENGTH: 19
(B) TYPE: NUCLEOTIDE
(C) STRANDEDNESS: SINGLE
(D) TOPOLOGY: LINEAR (i i) MOLECULE TYPE: OLIGONUCLEOTIDE (i x) FEATURE:
(A) NAME/KEY:
(B) LOCATION:
(C) IDENTIFICATION METHOD:
(D) OTHER INFORMATION: TYPE C Beta C, POSITION 58

(x i) SEQUENCE DESCRIPTION: SEQ ID NO:63:

TCTGCTTCTG ATGGCTCAA                                                           19